United States Patent [19]
Wang et al.

[11] Patent Number: 6,083,703
[45] Date of Patent: Jul. 4, 2000

[54] IDENTIFICATION OF TRP-2 AS A HUMAN TUMOR ANTIGEN RECOGNIZED BY CYTOTOXIC T LYMPHOCYTES

[75] Inventors: Rong Fu Wang, Bethesda; Steven A. Rosenberg, Potomac, both of Md.

[73] Assignee: The United States of America as represented by the Department of Health and Human Services, Washington, D.C.

[21] Appl. No.: 09/162,368

[22] Filed: Sep. 28, 1998

Related U.S. Application Data

[60] Division of application No. 08/725,736, Oct. 4, 1998, Pat. No. 5,831,016, which is a continuation-in-part of application No. 08/599,602, Feb. 9, 1996, Pat. No. 5,840,839.

[51] Int. Cl.$^7$ ............... C12Q 1/68; C12N 1/13; C12N 15/12; C12N 15/63; C12P 21/02
[52] U.S. Cl. ............ 435/6; 435/69.3; 435/252.3; 435/252.33; 435/320.1; 435/325; 536/23.1; 536/23.5
[58] Field of Search ............ 435/6, 69.1, 69.3, 435/252.3, 254.11, 325, 320.1; 424/277.1; 536/23.1, 23.5, 24.31, 24.33

[56] References Cited

U.S. PATENT DOCUMENTS 5,831,016  11/1998  Wang et al. ............ 530/350

FOREIGN PATENT DOCUMENTS

WO 91/14775  10/1991  WIPO .
WO 94/03205   2/1994  WIPO .
WO 95/23814   9/1995  WIPO .

OTHER PUBLICATIONS

Bloom et al, "Identification of Tyrosinase–related Protein 2 as a Tumor Rejection Antigen for the B16 Melanoma", *The Journal of Experimental Medicine,* vol. 185, No. 3, Feb. 3, 1997, pp. 453–459.

Cohen et al, "Nucleotide sequence of the cDNA encoding human tyrosinase–related protein", NucleicAcids Research, vol. 18, No. 9, May 11,1990, pp. 2807–2808.

Vijayasaradhi et al, "The Melanoma Antigen gp75 Is The Human Homologue fo the Mouse b (Brown) Locus Gene Product", *The Journal of Experimental Medicine,* vol. 171, No. 4, Apr. 1, 1990, pp. 1375–1380.

Wang et al, "Identification of TRP–2 as a Human Tumor Antigen Recognized by Cytotoxic T Lymphocytes", *The Journal of Experimental Medicine,* vol. 184, Dec. 1996, pp. 2207–2216.

Orlow et al, "Changes in expression of putative antigens encoded by pigment genes in mouse melanomas at different stages of malignant progression", *Proc. Natl. Acad. Sci. USA,* vol. 92, pp. 10152–10156, Oct. 1995.

Hara et al, "Implicating a Role for Immune Recognition of Self in Tumor Rejection: Passive Immunization against the Brown Locus Protein",*J. Exp. Med.*, vol. 182, Nov. 1995, pp. 1609–1614.

Malarkannan et al, "A Rare Cryptic Translation Product Is Presented by $K^b$ Major Histocompatibility Complex Class I Molecule to Alloreactive T Cells" *J. Exp. Med.*, vol. 182, Dec. 1995, pp. 1739–1750.

Quelle et al, "Alternative Reading Frames of the INK4a Tumor Suppressor Gene Encode Two Unrelated Proteins Capable of Inducing Cell Cycle Arrest", *Cell*, vol. 83, pp. 993–1000, Dec. 15, 1995.

Uenaka et al, Identification of a Unique Antigen Peptide pRL1 on BALB/c RL♂1 Leukemia Recognized by Cytotoxic T Lymphoycytes and Its Relation to the Akt Oncogene, *J. Exp. Med.*, vol. 180, Nov. 1994, pp. 1599–1607.

Salgaller et al, "Immunization against Epitopes in the Human Melanoma Antigen gp100 following Patient Immunization with Synthetic Peptides", *Cancer Research*, 56, pp. 4749–4757, Oct. 15, 1996/.

Wang et al, "Human tumor antigens recognized by T lymphocytes: implications for cancer therapy", Journal of Leukocyte Biology, vol. 60, Sep. 1996, pp. 296–309.

Wang et al, "Utilization of an Alternative Open Reading Frame of a Normal Gene in Generating a Novel Human Cancer Antigen", *The Journal of Experimental Medicine*, vol. 183, Mar. 1993, pp. 1131–1140.

Kawakami et al, "Identification of the Immunodominant Peptides of the MART–1 Human Melanoma Antigen Recognized by the Majority of HLA–A2–restricted Tumor Infiltrating Lymphocytes", The Journal of Experimental Medicine, vol. 180, Jul. 1994, pp. 347–352.

Brichard, et al., "The Tyrosinase Gene Codes for an Antigen Recognized by Autologous Cytolytic T. Lymphocytes on HLA–A2 Melanomas", *J. Exp. Med.*, 1993, 178:489–495.

Robbins, et al., "Recognition of Tyrosinase by Tumor–infiltrating Lymphocytes from a Patient responding to Immunotherapy",*Cancer Res.*, 1994, 54:3124–3126.

Wang et al., "Identification of a Gene Encoding a Melanoma Tumor Antigen Recognized by HLA–A31–restricted Tumor–infiltrating Lymphocytes", *J. Exp. Med.*, 1995, 181:799–804.

Topalian, et al., "Melanoma–specific CD4+ T Cells Recognized Nonmutated HLA–DRA–restricted Tyrosinase Epitopes", *J. Exp. Med.*, 1996, 183:1965–1971.

(List continued on next page.)

*Primary Examiner*—Robert A. Schwartzman
*Attorney, Agent, or Firm*—Morgan & Finnegan, L.L.P.

[57]  ABSTRACT

The infusion of TIL586 along with interleukin-2 (IL-2) into the autologous patient with metastatic melanoma resulted in the objective regression of tumor. A gene encoding a tumor antigen recognized by TIL586 was previously isolated and shown to encode gp75 or TRP-1. The present invention relates to the identification of a second tumor antigen recognized by a HLA-A31 restricted CTL clone derived from the TIL586 cell line. This antigen derived from the TRP-2 protein tumor antigen and peptides thereof are capable of sensitizing target cells for lysis by a CTL clone at 1 nM peptide concentration. Modified peptides were also recognized by the CTL clone.

27 Claims, 5 Drawing Sheets

OTHER PUBLICATIONS

Schadendorf et al., "Metastatic potential of human melanoma cells in nude mice—characteristics of phenotype, cytokine secretion and tumour–associated antigen", *Brit. J. Cancer*, 1996, 74:194–199.

Houghton, "Cancer Antigens Immune Recognition of Self and Altered Self", *J. Exp. Med.*, 1994, 180:1–4.

Kawakami, et al., "Human Melanoma Antigens Recognized by T. Lymphocytes",*Keio J. Med.*, Jun.1996 45(2):100–108.

Yokoyama, et al.,"Molecular cloning and functional analysis of a cDNA coding for human DOPAchrome tautomerase/tyrosinase–related protein–2" *Biochim. Biophys. Acta*, 1994, 1217:317–321.

Bouchard, et al., "Molecular characterization of a human tyrosinase–related protein–2 cDNA" *Eur. J. Biochem.*, 1994, 219:127–134.

Bouchard, et al., "Production and Characterization of Antibodies Against Human Tyrosinase", *The Journal for Investigative Dermatology*, 1994, 102:291–295.

Cassady, et al., "Sequence of the human dopachrome tautomerase–encoding TRP–2 cDNA" *Gene*, 1994, 143:295–298.

Tsukamoto, K. et al., "A second tyrosinase–related protein, TRP–2,is a melanogenic enzyme termed DOPAchrome tautomerase" *The EMBO Journal*, 1992, 11:519–529.

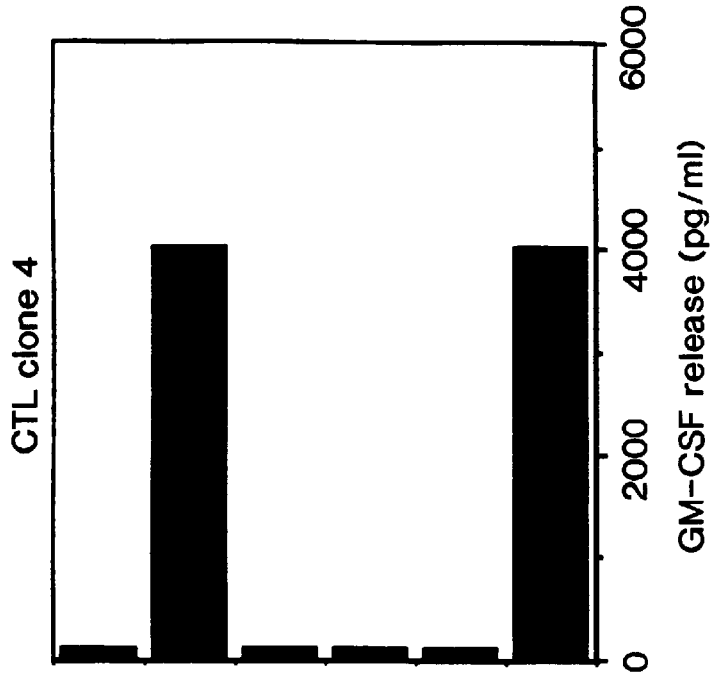
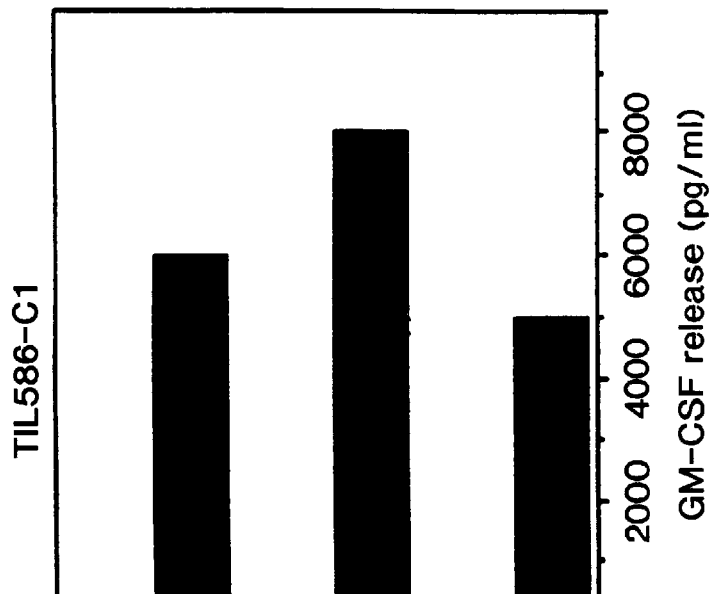
FIG. 1A
FIG. 1B

```
GCAATTAAAGTCAAGAGCTAAGGAGGGAGGGAGAGGGTTTAGAAATACCAGCATAATAAG
TAGTATGACTGGGTGCTCTGTAAATTAACTCAATTAGACAAAGCCTGACTTAACGGGGGA
AGATGGTGAGAAGCGCTACCCTCATTAAATTTGGTTGTTAGAGGCGCTTCTAAGGAAATT
AAGTCTGTTAGTTGTTTGAATCACATAAAATTGTGTGTGCACGTTCATGTACACATGTGC
ACACATGTAACCTCTGTGATTCTTGTGGGTATTTTTTTAAGAAGAAAGGAATAGAAAGCA
 AAGAAAAATAAAAAATACTGAAAAGAAAAGACTGAAAGAGTAGAAGATAAGGAGAAAAGT
ACGACAGAGACAAGGAAAGTAAGAGAGAGAGAGAGCTCTCCCAATTATAAAGCCATGAGC
                                                     M   S
CCCCTTTGGTGGGGGTTTCTGCTCAGTTGCTTGGGCTGCAAAATCCTGCCAGGAGCCCAG
  P   L   W   W   G   F   L   L   S   C   L   G   C   K   I   L   P   G   A   Q
GGTCAGTTCCCCCGAGTCTGCATGACGGTGGACAGCCTAGTGAACAAGGAGTGCTGCCCA
    G   Q   F   P   R   V   C   M   T   V   D   S   L   V   N   K   E   C   C   P
CGCCTGGGTGCAGAGTCGGCCAATGTCTGTGGCTCTCAGCAAGGCCGGGGGCAGTGCACA
    R   L   G   A   E   S   A   N   V   C   G   S   Q   Q   G   R   G   Q   C   T
GAGGTGCGAGCCGACACAAGGCCCTGGAGTGGTCCCTACATCCTACGAAACCAGGATGAC
    E   V   R   A   D   T   R   P   W   S   G   P   Y   I   L   R   N   Q   D   D
CGTGAGCTGTGGCCAAGAAAATTCTTCCACCGGACCTGCAAGTGCACAGGAAACTTTGCC
    R   E   L   W   P   R   K   F   F   H   R   T   C   K   C   T   G   N   F   A
GGCTATAATTGTGGAGACTGCAAGTTTGGCTGGACCGGTCCCAACTGCGAGCGGAAGAAA
    G   Y   N   C   G   D   C   K   F   G   W   T   G   P   N   C   E   R   K   K
CCACCAGTGATTCGGCAGAACATCCATTCCTTGAGTCCTCAGGAAAGAGAGCAGTTCTTG
    P   P   V   I   R   Q   N   I   H   S   L   S   P   Q   E   R   E   Q   F   L
                 pTD4
GGCGCCTTAGATCTCGCGAAGAAGAGAGTACACCCCGACTACGTGATCACCACACAACAC
    G   A   L   D   L   A   K   K   R   V   H   P   D   Y   V   I   T   T   Q   H
           Apa I                                       Pst I
TGGCTGGGCCTGCTTGGGCCCAATGGAACCCAGCCGCAGTTTGCCAACTGCAGTGTTTAT
    W   L   G   L   L   G   P   N   G   T   Q   P   Q   F   A   N   C   S   V   Y
                     pTA
GATTTTTTTGTGTGGCTCCATTATTATTCTGTTAGAGATACATTATTAGGACCAGGACGC
    D   F   F   V   W   E   H   Y   Y   S   V   R   D   T   L   L   G   P   G   R
                                                     pTD3     Kpn I
CCCTACAGGGCCATAGATTTCTCACATCAAGGACCTGCATTTGTTACCTGGCACCGGTAC
    P   Y   R   A   I   D   F   S   H   Q   G   P   A   F   V   T   W   H   R   Y
                                                                     pTK
CATTTGTTGTGTCTGGAAAGAGATCTCCAGCGACTC......ACAGAAGAAGCCTAG 1975
    H   L   L   C   L   E   R   D   L   Q   R   L       T   E   E   A   STOP
```

IDENTIFICATION OF TRP-2 AS A HUMAN TUMOR ANTIGEN RECOGNIZED BY CYTOTOXIC T LYMPHOCYTES

This is a divisional application Ser. No. 08/725,736 filed Oct. 4, 1998, U.S. Pat. No. 5,831,016, herein incorporated by reference, which is a continuation-in-part application of U.S. application Ser. No. 08/599,602 filed Feb. 9, 1996, U.S. Pat. No. 5,840,839, which is incorporated herein by reference.

FIELD OF THE INVENTION

The present invention relates to a cancer vaccine. In addition, the present invention relates to the area of human cancer diagnostics and therapeutics. More specifically, the invention relates to the isolation and purification of a novel tumor antigen capable of acting as a tool in treating and preventing cancer and a DNA sequence encoding the cancer antigen. The invention further relates to novel cancer peptides from within the tyrosinase-related protein 2 (TRP 2). The invention further relates to methods of detecting, diagnosing, treating and preventing cancer and precancer in an individual.

BACKGROUND OF THE INVENTION

The adoptive transfer of tumor infiltrating lymphocytes (TIL) plus interleukin-2 (IL-2) into the autologous patient with metastatic melanoma can result in the objective regression of tumor (Rosenberg et al. (1988); Rosenberg et al. (1994)), suggesting that T cells play an important role in tumor rejection in vivo. To understand the molecular basis of T cell-mediated antitumor responses, effort has been directed toward the identification of tumor antigens recognized by T cells and has led to the identification of a number of genes encoding tumor antigens in human melanoma (Boon et al. (1994); Houghton (1994); Tsomides et al. (1994); Pardoll (1994); Rosenberg (1995); Wang et al. (1996a)). These antigens can be divided into several classes based on their expression pattern. The tumor antigens such as MAGE1, MAGE3, BAGE and GAGE are encoded by genes that are expressed only in tumor, testis and placenta, but not other normal human tissues are examples of this class (Van der Bruggen et al. (1991); Gaugler et al. (1994); Van Den Eyne et al. (1995); Boel et al. (1995)). The second class of antigens such as MART-1/Melan-A (Kawakami et al. (1994a); Coulie et al. (1994)), gp100 (Kawakami et al. (1994b)), tyrosinase (Brichard et al. (1993); Robbins et al. (1994)) and gp75/TRP-1 (Wang et al. (1995)) are differentiation antigens encoded by genes that are expressed only in melanocytes, melanomas, and normal retinal tissue. These latter antigens are non-mutated self proteins. However, several mutated antigens were also identified to be recognized by T cells, including CDK4 (Wolfe et al. (1995)), β-catenin (Robbins et al. (1996)) and MUM-1 (Coulie et al. (1995)).

Recently, the gp75 TRP-1 gene encoding a tumor antigen recognized by the HLA-A31 restricted TIL586 was cloned (Wang et al. (1995)), which was previously shown to have in vivo antitumor activity when infused along with IL-2 into the autologous patient with melanoma. Surprisingly, the peptide recognized by TIL586 was found to be derived from the gene product translated from an alternative open reading frame of the TRP-1 gene (Wang et al. 1996b)). Site-directed mutagenesis experiments indicated that the ATG start codon in the alternative open reading frame was essential for generating the epitope recognized by TIL586. Six of fifteen T cell clones established from the TIL586 cell line were capable of recognizing 586mel tumor cells as well as 586EBV B cells pulsed with the peptide ORF3P derived from the alternative open reading frame of the TRP-1 gene (Wang et al. (1996b)). However, some T cell clones isolated from the same TIL586 line did not recognized TRP-1 and its ORF3P peptide pulsed on 586EBV B cells, although they were capable of recognizing 586mel and A31+ melanocytes.

One object of the present invention relates to the identification of TRP-2 as a new tumor antigen recognized by T cells.

Another object of the present invention are peptide fragments of TRP-2 and variants thereof, which function as cancer peptides.

Yet another object of the present invention are nucleic acid sequences encoding TRP-2 and fragments thereof, which, when expressed in a cell produce tumor antigens.

Another object of the present invention is a pharmaceutical composition comprising TRP-2 peptides which stimulate T-cells to elicit an immunogenic response against tumors and cancers.

Yet another object of the present invention is a method of using the tumor antigen and cancer peptide(s) as a pharmaceutical composition for the prevention, detecting and treatment of cancers.

It is still another object of the invention to provide a method for diagnosing human pre-neoplastic and neoplastic cells and tissues.

SUMMARY OF THE INVENTION

The tumor antigen of the present invention and the antigenic cancer peptides of the tumor antigen are encoded by all or a portion of the TRP-2 gene (SEQ ID NO:1). TRP-2 is a member of the tyrosinase related gene family. TRP-2 is presently identified as a new and potent tumor antigen capable of causing T cells to elicit an immune response.

One aspect of the invention are cancer peptides encoded by the TRP-2 gene or variants thereof, which are useful as a cancer vaccine capable of protecting the recipient from development of cancer. The present invention also relates to a method of administering the cancer vaccine in an effective amount to prevent cancers.

Another aspect of the present invention is a pharmaceutical composition comprising the TRP-2 tumor antigen alone or in combination with one or more co-immunostimulatory molecules. The tumor antigen may be provided as an immunogen or as a vaccine for prevention or treatment of cancer. The pharmaceutical composition is useful in methods of treating or preventing cancer in a mammal. In the method of treatment, the pharmaceutical composition is administered to the mammal in an amount effective in preventing or inhibiting the cancer in the mammal.

The present invention further provides vectors comprising the TRP-2 gene or portions thereof encoding the tumor antigen alone or in combination with a second DNA sequence encoding at least one co-immunostimulatory molecule. The vectors and host cells may serve as vaccines in which expression of a tumor antigen or cancer peptides results in the stimulation of tumor antigen specific T lymphocytes in a mammal immunized with the vaccine.

The invention provides a method of diagnosis cancer or precancer in a mammal by detection of the TRP-2 tumor antigen, wherein the tumor antigen, cancer peptide or variant thereof is recognized by T lymphocytes.

The invention also provides host cells transfected or transduced with a vector comprising DNA encoding a TRP-2 tumor antigen or variant thereof alone or in combination with a second DNA sequence encoding at least one co-immunostimulatory molecule.

The vectors and host cells may serve as vaccines in which expression of a TRP-2 tumor antigen results in the stimulation of antigen specific T lymphocytes in a mammal immunized with the vaccine.

The invention provides a method of diagnosis cancer or precancer in a mammal by detection of the tumor antigen encoded by the TRP-2 gene or fragments thereof wherein the tumor antigen is recognized by T lymphocytes.

Still another object of the invention is to provide a transgenic animal which has incorporated into its genome one or more copies of the tumor antigen of the present invention thereof. The incorporation of the TRP-2 DNA sequence or fragment thereof results in overexpression or expression of the tumor antigen. Such transgenic animals are useful for screening of therapeutic agents useful in treating cancer.

Still another aspect of the invention are monoclonal and polyclonal antibodies reactive with the TRP-2 tumor antigen, for use in diagnostic and detection assays. The monoclonal and polyclonal antibodies may be provided in the form of a kit alone, or along with other reagents commonly used in diagnostic and detection assays.

BRIEF DESCRIPTION OF THE DRAWINGS

These and other objects, features, and many of the attendant advantages of the invention will be better understood upon a reading of the following detailed description when considered in connection with the accompanying drawings:

FIG. 1A and 1B. Recognition of various target cells and the antigenic peptide by CTL clones derived from TIL586. T cell clones were generated by limiting dilution (1 cell per well) from the TIL586 cell line and were further expanded in AIM-V medium containing 6000 IU /ml IL-2. GM-CSF secretion by CTL clone 586TIL-C1 and clone 4 was measured after coculturing with normal melanocyte cell line (HLA-A31+), 586EBV B cells pulsed with the ORF3P peptide or irrelevant peptide, 397mel or 586mel cells.

FIG. 4. Antigenic peptide and partial coding sequence of TRP-2. The partial nucleotide and amino acid sequences (SEQ ID NOS: 1 and 2 respectively) of the TRP-2 gene are shown. The length and 3' terminus of the DNA fragments in pTD4, pTA, pTD3 and pTK are indicated by arrows and the restriction sites for Apa I, Pst I and Kpn I are marked. The antigenic peptide sequence recognized by CTL clone 4 is in bold and underlined.

Figure 2:
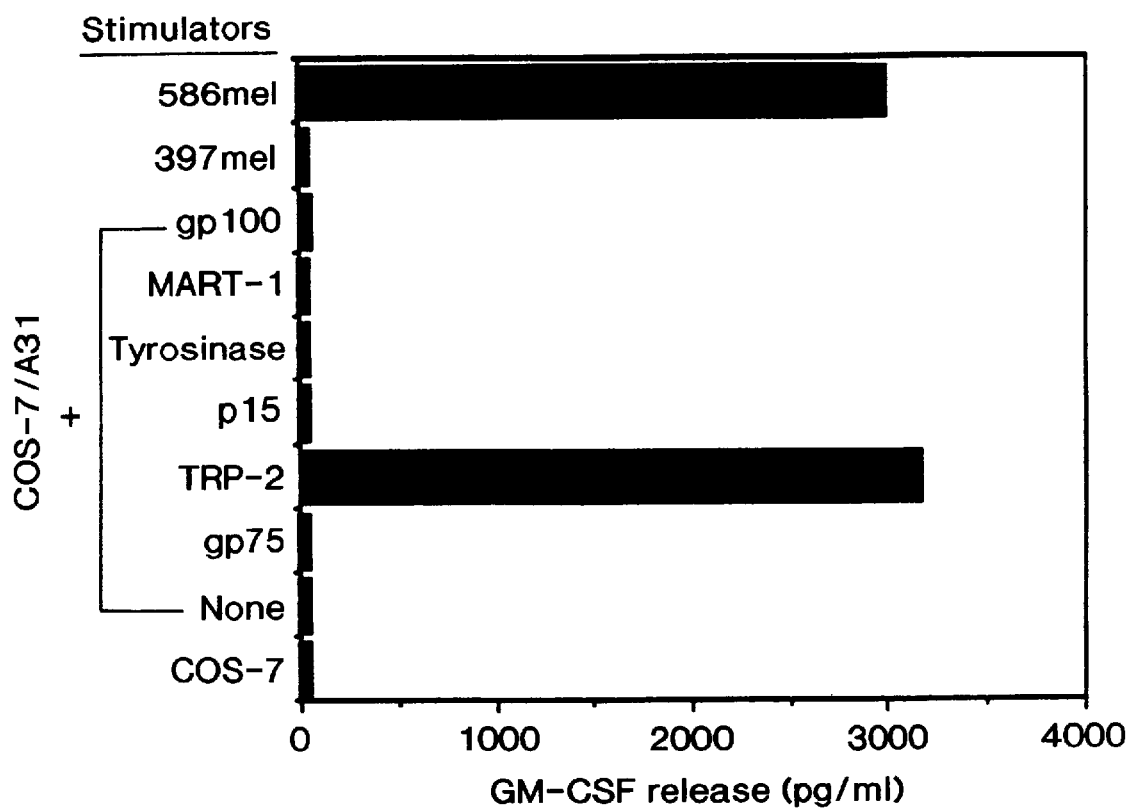
FIG. 2. Identification of TRP-2 as a new tumor antigen recognized by CTL clone 4. GM-CSF release by CTL clone 4 was measured after co-culture with COS-7 co-transfected with the HLA-A31 cDNA along with genes encoding MART-1, gp75/TRP-1, gp100, tyrosinase, p15 and TRP-2. Control stimulator cells included 586mel, 397mel, COS-7 alone, and COS-7 transfected the HLA-A31 cDNA.

(5B). Sensitization of the target cells for lysis by CTL clone 4 at different peptide concentrations. 586EBV B cells were incubated with $TRP_{197-205}$ (—▲—), an irrelevant peptide ORF3P (--Δ--), and T2 cells pulsed with $TRP_{197-205}$ (—●—) at various peptide concentrations. After peptide incubation, target cells were labelled for 30 min. Following washes, cytolytic activity of CTL clone 4 at an E:T ratio of 40:1 was measured after a 4 h incubation of T cells with target cells.

(5C). Lysis of the target cells by CTL clone 4 at the different E:T ratios. Target 586EBV cells were separately incubated with $TRP_{197-205}$, (—▲—) or the irrelevant peptides ORF3P (--Δ--) and target T2 cells were incubated with the $TRP_{197-205}$ peptide (—●—) for 90 min. 586mel (—□—) and 397mel (—■—) were used as positive and negative controls, respectively.

DETAILED DESCRIPTION OF THE INVENTION

The present invention encompasses a new tumor antigen, cancer peptides and variants thereof which are immunologically recognized by T lymphocytes of the immune system. The present invention further encompasses the antigen cancer epitope(s) which are contained in the tumor antigen. The antigenic cancer epitope specifically causes a cellular mediated immune response by interaction with T cells of the immune system. This interaction between the antigenic cancer epitope and the T cells causes the T cells to respond against, and prevent, eliminate or reduce the cancer in a mammal, including humans.

The cancer peptides and the antigenic cancer epitope contained within the tumor antigen of the present invention are derived from the TRP-2 protein, which is expressed primarily in melanomas, normal melanocyte cell lines and retina. The tumor antigen of the present invention present in significantly lower levels in most normal cells than the elevated levels found in pre-cancer and cancer cells. Elevated expression of the tumor antigen correlates with transformation of normal cells to a pre-cancer or cancer cell. TRP-2 is located on the human chromosome 13 and has been shown to be a member of the tyrosinase-related gene family and shares a 40–45% amino acid sequence identity to tyrosinase and gp75/TRP-1 (Yokoyama et al. (1994); Bouchard, et al. (1994)). TRP-2 encodes a protein with 519 amino acids and has been demonstrated to have DOPAchrome tautomerase activity involved in melanin synthesis (Bouchard et al. (1994)).

The tumor antigen of the present invention form part of, or are derived from, cancers including but not limited to primary or metastatic melanoma, thymoma, lymphoma, sarcoma, lung cancer, liver cancer, non-Hodgkin's lymphoma, Hodgkins lymphoma, leukemias, uterine cancer, cervical cancer, bladder cancer, kidney cancer and adenocarcinomas such as breast cancer, prostate cancer, ovarian cancer, pancreatic cancer, and the like.

The term "melanoma" includes, but is not limited to, melanomas, metastatic melanomas, melanomas derived from either melanocytes or melanocyte related nevus cells, melanocarcinomas, melanoepitheliomas, melanosarcomas, melanoma in situ, superficial spreading melanoma, nodular melanoma, lentigo maligna melanoma, acral lentiginous melanoma, invasive melanoma or familial atypical mole and melanoma (FAM-M) syndrome.

The "tumor antigen" of the present invention encompasses the TRP-2 protein and any portion or peptide of the TRP-2 protein capable of eliciting an anti-tumor response in mammals, including the full-length TRP-2 protein.

"Cancer peptides" as the term is used herein, encompasses any epitope or fragment of TRP-2 protein, which acts as a tumor antigen.

"Fragment" as the term is used herein means any segment of a protein or gene, having at least 5 or 6 amino acids in the case of a protein fragment and at least 15–18 nucleotides in the case of a gene.

Of particular interest are cancer peptides of TRP-2, or variants thereof recognized by autologous CTL in patients with cancer, in particular melanoma. Of further interest are cancer peptides, fragments or derivatives thereof recognized by MHC restricted CTL, in particular MHC class I restricted CTLs. A preferred HLA subtype recognized by the cancer peptides are the HLA-A31 subtype. The present invention relates to the identification of TRP-2, a melanoma/melanocyte differentiation antigen of the tyrosinase protein family, as a potent tumor antigen recognized by HLA-A31 restricted T cells. The TRP-2 gene product is the second tumor antigen recognized by CTL clones isolated from TIL586.

In one embodiment, the tumor antigen of the present invention comprises one or more antigenic cancer epitopes immunologically recognized by tumor infiltrating lymphocytes (TIL) derived from a cancer tumor of a mammal. Of particular interest are antigenic cancer epitopes recognized by cancer antigen specific cytotoxic T cells (CD 8$^+$).

In another embodiment of the present invention the tumor antigen is a cancer peptide comprising about 9 amino acids and is expressed from the gene that encodes tyrosinase-related protein-2 (SEQ ID NO:1) or from homologs or variants thereof depicted in FIG. 4.

In yet another embodiment, fragments of the TRP-2 protein or functionally equivalent variants thereof are used as cancer peptides. Preferably, the tumor antigen of the present invention comprises fragments of the TRP-2 protein containing at least a portion of amino acids 197–205. Most preferably, the cancer peptide of the present invention comprises the amino acid sequence: LLGPGRPYR (SEQ ID NO:4) and fragments, or derivatives thereof. Also encompassed in the ambit of the invention are cancer peptides or portions thereof that share partial sequence homology with the region of TRP-2 containing amino acids 197–205. By partial amino acid sequence homology is meant a peptide having at least 85% sequence homology with LLGPGRPYR (SEQ ID NO:4), preferably at least 95% sequence homology or greater and has the biological function of stimulating cancer antigen specific T lymphocytes.

The present invention relates to functionally equivalent variants of the TRP-2 cancer peptides. "Functionally equivalent variants" includes peptides with partial sequence homology, peptides having one or more specific conservative and/or non-conservative amino acid changes, peptide conjugates, chimeric proteins, fusion proteins and peptide nucleic acids.

Another embodiment of the present invention encompasses cancer peptides having sufficient homology to LLG-PGRPYR (SEQ ID NO:4) to effectively act as cancer peptides. Such peptides may have conservative amino acid changes at one or more positions. By conservative amino acid changes is meant, an amino acid change at a particular position which is of the same type as originally present; i.e. a hydrophobic amino acid exchanged for a hydrophobic amino acid, a basic amino acid for a basic amino acid, etc. Such amino acid changes do not significantly alter the overall charge and configuration of the peptide and therefore such variants maintain the anti-cancer activity of a cancer peptide. Examples of such conservative changes are well-known to the skilled artisan and are within the scope of the present invention.

Yet another embodiment of the present invention relates to several cancer peptides which are derived from the LLGPGRPYR (SEQ ID NO:4) peptide, but contain non-conservative amino acid changes at one or more positions. Such peptides have been identified in the present invention and include, but art not limited to LSGPGRPYR (SEQ ID NO:9), KLGPGRPYR (SEQ ID NO:12), LLGPGFPYR (SEQ ID NO:13) and fragments and derivatives thereof.

The tumor antigen and the antigenic cancer epitopes thereof may be purified and isolated from natural sources such as from primary clinical isolates, cell lines and the like. The cancer peptides and their antigenic epitopes may also be obtained by chemical synthesis or by recombinant DNA techniques known in the arts. Techniques for chemical synthesis are described in Steward et al. (1969); Bodansky et al. (1976); Meienhofer (1983); and Schroder et al. (1965).

The tumor antigen and antigenic cancer epitopes thereof may be formulated with pharmaceutically acceptable carriers into pharmaceutical compositions by methods known in the art. The composition is useful as a vaccine to prevent or treat cancer. The composition may further comprise at least one co-immunostimulatory molecule. Co-immunostimulatory molecules to be used in conjunction with the tumor antigen of the present invention for stimulating antigen specific T cell responses include but are not limited to one or more major histocompatibility complex (MHC) molecules, such as class I and class II molecules, preferably a class I molecule. The composition may further comprise other stimulator molecules including B7.1, B7.2, ICAM-1, ICAM-2, LFA-1, LFA-3, CD72 and the like, and cytokines which include but are not limited to IL-1 through IL-15, TNFα, IFNγ, RANTES, G-CSF, M-CSF, IFNα, CTAP III, ENA-78, GRO, I-309, PF-4, IP-10, LD-78, MGSA, MIP-1α, MIP-1β, or combination thereof, and the like for immunopotentiation.

The stimulatory molecule may be provided as a physically separate entity or it may be provided in the membrane of an antigen presenting cell such as B-cell, macrophage or dendritic cell, in the membrane of a liposome, or expressed on the surface of a transduced or transfected cell. DNA sequences of MHC co-immunostimulatory molecules are available from DNA sequence repositories, such as GenBank and the like.

The tumor antigen of the present invention is useful in methods of preventing or treating cancer and useful in diagnostic assay for detecting cancer or precancer in a mammal, including humans. The tumor antigen, cancer peptides or variants thereof may be in the form of a derivative in which other constituents are attached thereto such as radiolabels, biotin, fluorescein. A targeting agent may also be attached to the tumor antigen or cancer peptides that allow for specific targeting to a specific organ, tumor or cell types. Such targeting agents may be hormones, cytokines, cellular receptors and the like. The tumor antigen of the present invention may be prepared in the form of a kit, alone or in combination with other reagents.

Another aspect of the invention is a vaccine useful in inducing tumor-specific cell-mediated immunity against cancer.

Approaches to cancer immunotherapy can be divided into active or passive categories. Active immunotherapy involves the direct immunization of cancer patients with cancer antigens in an attempt to boost immune responses against the tumor. Passive immunotherapy refers to the administration of immune reagents, such as immune cells or antibodies with antitumor reactivity with the goal of directly mediating antitumor responses.

Most prior attempts at active immunotherapy utilized either intact cancer cells or cancer cell extracts with the expectation that these materials contained tumor antigens in an amount and form capable of stimulating immune responses. The molecular identification of cancer antigens however, has open new possibilities for developing immunotherapies for the treatment of human cancer. A summary of some of these approaches is presented in Table A.

TABLE A

Cancer Therapies Based on the Molecular Identification of Cancer Antigens

1. Active immunotherapy with:
   a. Immunodominant peptides
      1) alone
      2) combined with adjuvants
      3) linked to helper peptides, lipids or liposomes
      4) pulsed onto antigen presenting cells
   b. Immunodominant peptides with amino acids substitutions to increase binding to MHC molecules
   c. Proteins alone or combined with adjuvants
   d. "Naked" DNA encoding cancer antigens
      1) "gene gun" for intradermal injection
      2) intramuscular injection
      3) linked to lipids
   e. Recombinant viruses such as vaccinia, fowlpox or adenovirus encoding
      1) cancer antigens alone
      2) cancer antigens plus genes encoding cytokines, costimulatory molecules, or other genes to enhance the immune response
   f. Recombinant bacteria such as BCG, Salmonella or Listeria encoding cancer antigens alone or in combination with co-immunostimulatory molecules
2. Active immunotherapy (above) followed by the administratino of co-immunostimulatory cytokines.
   1. IL-2
   2. IL-6
   3. IL-10
   4. IL-12

The insertion of the gene encoding cancer antigens into high efficiency expression systems such as *E. coli,* yeast or baculovirus and the like provides the opportunity to obtain large amounts of purified tumor antigen for use in immunization. Alternatively, the immunodominant peptides from these tumor antigens could readily be synthesized in vitro and purified in large amounts for immunization alone or in a form intended to improve their immunogenicity such as in combination with adjuvant, linkage to lipids/liposomes or helper peptides, or pulsed onto antigen presenting cells. Modification of individual amino acids of the immunodominant peptides to improve binding efficiency to MHC antigens can potentially increase immunogenicity compared to the native peptide.

Recent techniques utilizing "naked" DNA injected directly into muscle or into the skin have been shown to raise both cellular and humoral immune reactions to encoded antigens (Cooney, et al. (1991); Wolff et al. (1990); Davis et al. (1993); Yang, (1990); Williams (1991); Fynan et al. (1995); Eisenbraum et al. (1993); Fuller et al. (1994); Acsadi et al. (1991)). Techniques using non-viable DNA vectors have the advantage of ease of preparation and safety of administration. The alternative nucleic acid sequence of the present invention is useful as an immunogen and as a DNA vaccine against cancer. The DNA sequences encoding the TRP-2 proteins or peptides of the present invention may be administered using a gene gun in amounts to elicit a cellular response against a cancer cell. Nanogram quantities are useful for such purposes.

An effective form of immunization involves the incorporation of genes encoding immunogenic molecules into recombinant bacteria such as BCG, Salmonella or Listeria or into recombinant viruses such as vaccinea, fowlpox or adenovirus and the like. The genes encoding cancer antigens can be expressed either alone or in combination with genes encoding co-immunostimulatory molecules or other genes which can enhance the immune response following infection. Studies with model tumor antigens in murine models have shown that incorporation of the gene for interleukin-2 (IL-2) or B7.1 can increase the immunogenicity of model tumor antigens and even mediate the regression of established lung metastases bearing these antigens and even mediate the regression of established lung metastases bearing these antigens. Active immunotherapy followed by the exogenous administration of co-immunostimulatory cytokines such as IL-2, IL-6, IL-10, IL-12, or IL-15 may also be used to improve immune responses.

Passive immunotherapy with genetically modified immune cells (commonly referred to as adoptive immunotherapy) capable of recognizing human tumor antigens is effective in mediating the regression of cancer in selected patients with metastatic melanoma. In vitro techniques have been developed in which human lymphocytes are sensitized in vitro to tumor antigen immunodominant peptides presented on antigen presenting cells. By repetitive in vitro stimulation cells can be derived with a far greater capacity to recognize human tumor antigens than the TIL that were used to clone the genes encoding these antigens. Thus by repeated in vitro sensitization with the tumor antigen of the present invention, lymphocytes could be derived with 50 to 100 times more potency of TIL. The adoptive transfer of these cells may be more effective in mediating tumor regression in vivo than are conventionally grown TIL.

In the methods of preventing or inhibiting cancer, the tumor antigen, cancer peptides or variants thereof may be administered via one of several routes including but not limited to intravenous, intramuscular, subcutaneous, intradermal, intraperitoneal, intrathecal, intrapleural, intrauterine, rectal, vaginal, topical, intratumor and the like.

Administration may be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be by nasal sprays, for example, or suppositories. For oral administration, the tumor antigen, cancer peptides or variants thereof are formulated into conventional oral administration form such as capsules, tablets and toxics.

In general, it is desirable to provide the recipient with a dosage of tumor antigen or cancer peptide of at least about 1 pg per Kg body weight, preferably at least about 1 ng per Kg body weight, more preferably at least about 1 μg or greater per Kg body weight of the recipient. A range of from about 1 ng per Kg body weight to about 100 mg per Kg body weight is preferred although a lower or higher dose may be administered. The dose is effective to prime, stimulate and/or cause the clonal expansion of cancer antigen specific T lymphocytes, preferably cytotoxic T lymphocytes, which in turn are capable of preventing or inhibiting cancer in the recipient.

The dose is administered at least once and may be provided as a bolus or a continuous administration. Multiple administrations of the dose over a period of several weeks to months may be preferable. Subsequent doses may be administered as indicated.

In a method of treatment, a vaccine comprising the tumor antigen or one or more cancer peptides thereof is administered to a mammal in an amount effective to prevent cancer in the mammals. Of particular interest is a vaccine comprising one or more cancer peptides encoded by fragments of the TRP-2 gene for prevention of melanoma.

In a method of reducing tumor burden in animals, including humans, having tumors the method comprises administration of an effective amount of a antigenic cancer epitope at a site of tumor burden, said amount is effective to reduce the size of the tumor at the site.

In another method of treatment, autologous cytotoxic lymphocytes or tumor infiltrating lymphocytes may be obtained from a patient with cancer. The lymphocytes are grown in culture and cancer antigen specific lymphocytes expanded by culturing in the presence of the specific cancer peptides alone or in combination with at least one co-immunostimulatory molecule with cytokines. The antigen specific lymphocytes are then infused back into the patient in an amount effective to reduce or eliminate the tumors in the patient.

After immunization the efficacy of the vaccine can be assessed by production of immune cells that recognize the cancer antigen, as assessed by specific lytic activity, specific cytokine production, tumor regression or combination of these. If the mammal to be immunized is already afflicted with cancer or metastasis cancer the vaccine can be administered in conjunction with other therapeutic treatments such as immunomodulators, for example, IL-2, IL-6, IL-10, IL-12, IL-15, interferon, tumor necrosis factor and the like, chemotherapeutic drugs such as cisplatinum, antiviral such as gancyclovir, amphotericin B, antibiotics and the like.

One embodiment of the invention are portions of the TRP-2 encoding one or more cancer peptides. The gene sequence for TRP-2 has been disclosed through the Genbank under accession number D17547 as described by Yokoyama et al. (1994) and Genbank accession number S69231 as described by Bouchard et al. (1994).

In one embodiment, TRP-2 gene fragments encoding LLGPGRPYR (SEQ ID NO:4) and functionally equivalent sequence variants thereof for a cancer peptide recognized by cancer antigen specific T lymphocytes including tumor infiltrating lymphocytes. Also encompassed by the present invention are nucleic acid sequences complementary, as well as anticomplementary to a sequence encoding LLG-PGRPYR (SEQ ID NO:4) and equivalent sequence variants thereof.

In another embodiment, the DNA sequence encoding TRP-2 protein expresses all or more portions thereof. A preferred fragment of the TRP-2 gene comprises a region between a PstI site at nucleotide position 947 and a KpnI site at nucleotide position 1080.

Another preferred fragment of TRP-2 gene comprises: TTATTAGGACCAGGACGCCCCTACAGG (SEQ ID NO:15).

Due to degeneracy in the genetic code, variations in the DNA sequence will result in translation of equivalent cancer peptides. As a result, substitutions are included in the ambit of the invention as long as the substitution results in expression of a cancer peptide that is recognized by cancer antigen MHC-restricted T cells. Homologs from other mammalian species is included within the ambit of the invention.

All or part of the TRP-2 gene may be used as probes to identify and isolate the homologs of the cancer peptide in other mammalian species. In one embodiment, a murine cDNA sequence is used to screen a mammalian cDNA library for a human homolog nucleic acid sequence. Positive clones are selected and sequenced. Examples of tissue sources from which the cDNA library can be synthesized include but are not limited to dermis, epidermis, solid tumors, melanomas, melanocytes, and the like. One skilled in the art will understand the appropriate hybridization conditions to be used to detect the homologs. Conventional methods for nucleic acid hybridization construction of libraries and cloning techniques are described in Sambrook et al. (1989) and Ausubel et al. (1987).

Another aspect of the invention are nucleic acid probes for the detection and quantification of RNA that transcribes the TRP-2 tumor antigen in biologic samples isolated from a mammal with cancer. Alterations in the level of RNA relative to a control RNA sample is useful in diagnosis and prognosis of the disease in the mammal.

In one embodiment, TRP-2 mRNA is derived from tissue of a patient suspected of having cancer or precancer and compared with TRP-2 mRNA derived from a healthy control subject. A quantitative and/or qualitative increase of the TRP-2 mRNA in the patient, as compared to the control, is indicative of cancer or precancer in the patient. The mRNA may be detected using oligonucleotide probes.

Combinations of oligonucleotide pairs based on the sequence encoding the tumor antigen or cancer peptides thereof may be used as PCR primers to detect mRNA in biological samples using the reverse transcriptase polymerase chain reaction (RT-PCR) process for amplifying selected RNA sequences. The present invention also encompasses in situ PCR and in situ RT-PCR for detection of DNA and RNA encoding the cancer peptides or portions thereof. The technique is preferred when the copy number of a target nucleic acid is very low, or when different forms of nucleic acids must be distinguished. The method is especially useful in detecting and differentiating precancer and cancer cells from normal cells.

The present invention includes a method of identifying an antigenic cancer epitope reactive with antigen specific T cells comprising the generation of nucleic acid deletion fragments from a gene. The deletion fragments are placed in an appropriate vector which in turn are transfected or transduced into a host cell for the expression of the nucleic acid product. Optionally, the host cell may also express a co-immunostimulatory molecule. Cancer antigen specific T-cell responses are determined in the presence of the host cell expressing the deletion product.

In the case where the host cell expresses only the deletion product, a co-immunostimulatory molecule may be provided by an antigen presenting cell such as a B cell, macrophage, dendritic cell and the like or by a cell transfected with a stimulatory molecule. In one embodiment, the co-immunostimulatory molecule is a MHC class I molecule.

By mapping using this approach, the TRP-2 gene fragments encoding the cancer peptide or the antigenic cancer epitope is determined.

An alternative method of identifying the cancer antigen and the antigenic cancer epitope is by generating synthetic peptides, pulsing antigen presenting cells with the synthetic peptides and adding the peptide pulsed antigen presenting cells with antigen specific T cells and measuring the antigen specific response of T cells in the presence of the peptide pulsed antigen presenting cells. The synthetic peptides that result in antigen specific T cell responses contains the antigenic cancer epitope of the present invention.

The present invention also encompasses a vector comprising the TRP-2 gene and fragments thereof encoding the tumor antigen of the present invention. Optionally the vector may also comprise a DNA sequence encoding at least one co-immunostimulatory molecule.

Eukaryotic expression vectors include but are not limited to retroviral vectors, vaccinia virus vectors, adenovirus vectors, herpes virus vectors, fowlpox virus vectors, baculovirus vectors, human papillomavirus vectors, equine encephalitis vectors, influenza virus vectors and the like.

The present invention encompasses novel recombinant virus expressing the TRP-2 tumor antigen encoded by nucleic acid sequence of the TRP-2 gene or fragments or variant thereof. The recombinant virus may also express at least one co-immunostimulatory molecule. The recombinant virus is capable of eliciting or upregulating a cell-mediate immune response in a mammal for the purpose of preventing or treating cancer in the mammal, particularly humans.

The recombinant virus has incorporated into its genome or portion thereof a nucleic acid sequence encoding a TRP-2 tumor antigen or variant thereof, alone, or in combination with one or more genes encoding an co-immunostimulatory molecule. A host cell infected with the recombinant virus expresses a TRP-2 tumor antigen, alone or in combination with at least one co-immunostimulatory molecule.

Methods for constructing and expressing exogenous gene products from recombinant vaccinia virus vectors are disclosed by Perkus et al. (1985); Kaufman et al. (1991); Moss (1991); Smith et al. (1984); and U.S. Pat. No. 4,738,846. Sutter et al. (1992) disclose the construction and use as a vector, the non-replicating recombinant Ankara virus (MVA, modified vaccinia Ankara) which may be used as a viral vector in the present invention. Baxby et al. (1992) disclose the construction and use as a vector, a non-replicating poxvirus, including canarypox virus, fowlpox virus and other avian species for use as a viral vector in the present invention.

The vectors of the present invention may be placed in an appropriate host cell for the expression of the tumor antigen or antigenic cancer epitope. Eukaryotic host cell lines include, but are not limited to COS cells, CHO cells, Hela cells, NIH/3T3 cells, insect cells, antigen presenting cells such as dendritic cells and the like. Optionally the host cell may also express a stimulatory molecule. In the case where the host cells express the tumor antigen of the present invention in combination with at least one MHC molecule, it is preferable that a eukaryotic expression system be used to allow for proper glycosylation. The expression of both the cancer antigen and the co-immunostimulatory molecule by the host cell provides the necessary MHC restricted peptide to specific T cells and the appropriate signal to the T cell to aid in antigen recognition and proliferation or clonal expansion of antigen specific T cells. The overall result is an upregulation of the immune system. The upregulation of the immune response is manifest by an increase in cancer antigen specific cytotoxic lymphocytes which are able to kill or inhibit the growth of cancer or precancer cells.

The DNA may be inserted into the host cell by transfection, transduction, liposomes and the like by methods known in the art (Sambrook et al. (1989)). For liposomes, cationic lipids are preferred, for example, polycationic lipid, dimyristyloxypropyl-3-dimethyl-hydroxyethyl ammonium (DMRIE) complexed with the neutral phospholipid dioleoyl phosphatidyl-ethanolamine (DOPE) as disclosed by Nabel et al. (1992); Nabel et al. (1992a); Stewart et al. (1992); Nabel et al. (1993b); and Harrison et al. (1995).

The recombinant tumor antigen or antigenic cancer epitope expressed by the host cells may be purified from cell lysates or cell supernatants by standard protein purification procedures known in the art. These include but are not limited to molecular sieve chromatography, ion-exchange chromatography, isoelectric focusing, gel electrophoresis, affinity chromatography, HPLC, reverse phase HPLC and the like (Ausubel et al. (1987)). Immunoaffinity chromatography may also be used for purification using tumor antigen antibodies or antigen binding fragments thereof as described herein, as the immunoaffinity agent.

The recombinant virus may also be used as a therapeutic or vaccine. In such uses it is desirable to provide the recipient with a dosage of recombinant virus in the range of from about $10^5$ to about $10^{10}$ plaque forming units/mg mammal, although a lower or higher dose may be administered.

The recombinant viral vector may be introduced into a mammal either prior to any evidence of cancer such as melanoma or to mediate regression of the disease in a mammal afflicted with a cancer such as melanoma. Examples of methods for administering the viral vector into mammals include, but are not limited to, exposure of cells to the recombinant virus ex vivo, or injection of the recombinant virus into the affected tissue or intravenous, subcutaneous, intradermal, intramuscular and the like administration of the virus. Alternatively, the recombinant viral vector or combination of recombinant viral vectors may be administered locally by direct injection into the cancerous lesion or topical application in a suitable pharmaceutically acceptable carrier. The quantity of recombinant viral vector, carrying the nucleic acid sequence of interest is based on the titer of virus particles. A preferred range for immunization is about $10^5$ to $10^{10}$ virus particles per mammal, preferably a human.

Tumor infiltrating lymphocytes (TILs) derived from tumor-bearing patients recognize tumor associated antigens presented by major histocompatibility complex (MHC) class I molecules. The infusion of TIL586 along with interleukin-2 (IL-2) into the autologous patient with metastatic melanoma resulted in the objective regression of tumor. The present invention relates to a gene encoding a tumor antigen recognized by TIL586 and shown to encode TRP-2. The present invention also relates to the identification and isolation of an antigenic peptide, LLGPGRPYR (SEQ ID NO:4), derived from TRP-2 and active as a cancer vaccine.

The invention also provides a transgenic animal which has incorporated into its genome one or more copies of TRP-2 tumor antigen of the present invention. The general method of producing transgenic animals is described in Krimpenfort et al U.S. Pat. No. 5,175,384, Leder et al U.S. Pat. No. 5,175,383, Wagner et al U.S. Pat. No. 5,175,385, Evans et al U.S. Pat. No. 4,870,009 and Berns U.S. Pat. No. 5,174,986. The incorporation of the gene results in overexpression, altered expression or expression of multiple forms of the tumor antigen of the present invention. The resulting transgenic animal are useful in studies of the development of cancer. The animal model is useful in screening vaccines and chemotherapeutic drugs for cancer treatment.

This invention further comprises an antibody or antigen binding portion thereof elicited by immunization of the tumor antigen of the present invention. In the case where the cancer peptide is comprised of only a few amino acids, the cancer peptide may be conjugated to a carrier protein in order to elicite an antibody response. Carrier proteins such as KLH, tetanus toxoid and the like and methods of conjugation are known in the art. The antibody has specificity for and reacts or binds with the cancer peptide of the present invention.

Exemplary antibody molecules are intact immunoglobulin molecules, substantially intact immunoglobulin molecules or these portions of an immunoglobulin molecule that contain the antigen binding site, including those portions of immunoglobulin molecules known in the art as F (ab), F (ab'), F (ab')$_2$, humanized chimeric antibody, and F (v). Polyclonal or monoclonal antibodies may be produced by methods known in the art. (Kohler et al. (1975); Campbell (1985)). The antibodies or antigen binding fragments may also be produced by genetic engineering. The technology for expression of both heavy and light chain genes is the subject of the PCT patent applications: publication number WO 901443, WO 9014424, and Huse et al (1989).

In one embodiment, the antibodies of the invention are used in immunoassays to detect a TRP-2 tumor antigen in biological samples. The antibodies or antigen binding fragments thereof may be used to detect cancer peptides in tissue biopsy samples from a mammal afflicted with cancer. Assessment of the cancer antigen in a diseased tissue can be used to prognose the progression of the disease in a mammal or may diagnose the efficacy of a treatment. The immunoassay may be a radioimmunoassay, Western blot assay, immunofluorescent assay, enzyme immunoassay, chemiluminescent assay, immunohistochemical assay and the like and may be performed in vitro, in vivo or in situ. Standard techniques known in the art for ELISA are described by Rose et al. (1980); Campbell et al. (1964); and Oellerich (1984). Conventional methods for immunohistochemistry are described in Harlow et al. (1988); and Ausubel et al. (1987). Biological samples appropriate for such detection assays include but are not limited to cells, tissue biopsy, whole blood, plasma, serum, sputum, cerebrospinal fluid, pleural fluid, urine and the like.

The antibodies or antigen binding fragments of the present invention may also be used in immunotherapy. The antibodies or antigen binding fragment thereof is provided to a mammal in an amount sufficient to prevent, lessen or attenuate the severity, extent or duration of the cancer.

All articles and patents referred to herein are incorporated, in toto, by reference.

While the invention is described above in relation to certain specific embodiments, it will be understood that many variations are possible, and that alternative materials and reagents can be used without departing from the invention. In some cases such variations and substitutions may require some experimentation, but will only involve routine testing.

The foregoing description of the specific embodiments will so fully reveal the general nature of the invention and others can, by applying current knowledge, readily modify and/or adopt for various applications such specific embodiments without departing from the generic concept, and therefore such adaptations and modifications are intended to be comprehended within the meaning and range of equivalents of the disclosed embodiments.

EXAMPLE 1

Materials and Methods

Chemicals and Reagents

The following chemicals and reagents were purchased from the sources indicated: RPMI1640, AIM-V media, Lipofectarnine, G418 (GIBCO BRL, Gaithersberg, Md.); the eukaryotic expression vector pCR3 (Invitrogen, San Diego, Calif.); anti-HLA-A31 monoclonal antibody (One lambda, Canoga Park, Calif.); anti-immunoglobulin M antibody conjugated with fluorescein isothiocyanate (Vector Laboratories, Inc., Burlingame, Calif.).

T Cell Clones and Lines

The T cell clones were generated by limiting dilution methods (at 1 cells/well) from the TIL586 cell line, and used allogenic PBL ($1 \times 10^3$ cells/well) as feeder cells in RPMI1640 containing 10% human AB sera and 500 IU IL-2. After 12 days, T cell clones were then expanded in AIM-V medium containing 6000 IU/ml IL-2. To obtain an optimal expansion, we used the OKT3 expansion method described by S. Riddell (Walter et al. (1995)). Briefly, on day 0, $5 \times 10^4$ $5 \times 10^5$ T cells were cocultured with HLA-A31 PBL (500:1, PBL:T cell ratio) and 586EBV B cells (100:1, EBV:T cell ratio) in 25 ml RPMI 1640 containing 11% human sera, 30 ng/ml OKT3 antibody and antibiotics. On day 1, IL-2 was added at final concentration of 180 IU/ml. The media were changed with fresh media containing 11% human sera, IL-2 180 IU/ml on day 5. The media were then changed every three days. On day 12–14, T cells were harvested, counted and cryopreserved. TIL586 were isolated from the tumor specimen of a patient with metastatic melanoma and grown in medium containing IL-2 (6000 IU/ml) (Chiron) for 32–60 days as previously described [Topalian et al. 1988). TIL586 were predominantly CD8$^+$T cells.

Melanoma cell lines 397mel, 397mel/A31, 586mel, 624mel, 624mel/A31 and EBV transformed B-cell lines 586EBV and 1510EBV were established in our laboratory and cultured in RPMI 1640 medium containing 10% fetal calf serum (FCS). Normal cultured melanocytes derived from infant foreskin (NHEM680 purchased from Clonetics, Calif.) were cultured in melanocyte growth medium (MOM; Clonetics, Calif.). The COS-7 cell line was provided by Dr. W. Leonard (NIH).

GM-CSF Secretion Assay

DNA transfection and GM-CSF assays were performed as previously described (Wang et al. 1995). Briefly, 200 ng of DNA encoding antigens and 50 ng of the HLA-A31 DNA were mixed with 2 $\mu$l of lipofectamine in 100 ml of DMEM for 15–45 min. The DNA/lipofectamine mixture was then added to the COS-7 (5×104) cells and incubated overnight. The following day, cells were washed twice with DMEM medium. TIL586 was added at a concentration of 1×105 cells/well in AIM-V medium containing 120 IU/ml of IL-2. For T cell clones, only 1–2×10$^4$ cells/well were added. After 18–24 h incubation, 100 $\mu$l of supernatant was collected and GM-CSF was measured in a standard ELISA assay (R+D Systems, Minneapolis, Minn.). For testing peptides recognition, 586EBV or T2 cells were incubated with peptides at 37° C. for 90 min, and then washed three times with AIM-V medium containing 120 IU/ml of IL-2. T cells were added and incubated for an additional 18–24 h, 100 µl of supernatant was collected for GM-CSF assay.

Exo III/SI Deletion Constructions and Subcloning

TRP-2 cDNA was a gift of Dr. Shibahara (Yokoyama et al. (1994)) and subcloned into the pCR3 vector with a CMV promoter for expression. To make a series of deletions, the plasmid pCR3 containing TRP-2 cDNA was digested with Xba I and filled in with alpha-phosphorothioate deoxyribonucleotide triphosphates to block Exo III nuclease digestion. The linearized DNA was subjected to the second restriction enzyme digestion to generate one end sensitive to Exo III Exo III nuclease/Mung bean nuclease deletion was performed according to the manufacture's instructions (Stratagene, Calif.). All deletion constructs were sequenced to determine the location of DNA sequence being removed. pTA plasmid was a derivative of pCR3-TRP2, in which an Apa I DNA fragment was deleted from the 3' end of TRP-2 gene. pTK was created after removal of a KpnI DNA fragment from the 3' end of the TRP-2 gene. pTP was generated by deleting an internal Pst I fragment and religation.

Northern Blot Analysis

Total RNA was isolated by the guanidine isothiocyanate/cesium chloride centrifugation method. Total RNA from human normal tissue was purchased from Clontech, Calif. Twenty µg of total RNA was subjected to electrophoresis in a 1.2% agarose formaldehyde gel and transferred to a nylon membrane. A 2.0 kb DNA fragment of the TRP-2 gene was labeled with $^{32}$P-α-CTP by the random priming method. Prehybridization and hybridization were performed according to the QuickHyb protocol (Stratagene). Membranes were washed twice with 2×SSC/0.1% SDS at room temperature for 15 min and twice with 0.1×SSC/0.1% SDS at 60° C. for 30 min. The autoradiography was performed at −70° C.

Cytotoxicity Assays

Cytolysis was determined by use of Calcein AM (Molecular Probes, Eugene, Oreg.). Briefly, T2 or 586EBV B cells were pulsed with peptides in RPMI1640/5%FCS for 90 min. Tumor cells and the peptide pulsed EBV B cells were labelled with Calcein AM (15 µl of 1 mg/ml Calcein AM for every 1×10$^6$ cells) for 30 min at 37° C. Following incubation, cells were washed three times with AIM V/120 IU IL-2. 1×10$^3$ target cells were mixed with T cells at various E:T ratio. After 4 h incubation at 37° C., 5 µl of bovine hemoglobin quench solution containing ethidium bromide was added. The plate was read by Lambda scan. The percentage of lysis was calculated from the following equation: $[1-(A-B)/(C-B)] \times 100$ where A is the reading of non-lysed cells in the presence of T cells, B is background signal value and C is the maximum signal value from target cells.

The peptides were synthesized by a solid-phase method using a peptide synthesizer (Model AMS 422, Gilson Co., Inc., Worthington, Ohio). Some peptides were purified by HPLC and had greater than 98% in purity. The peptide mass of some peptides was confirmed by mass spectrometry analysis.

EXAMPLE 2

Recognition of New Antigens on Tumor Cells by CTL Clones

In previous studies, we have isolated a number of T cell clones from the TIL586 cell line by the limiting dilution method (Wang et al. (1996b)). Among them, six clones recognized 586EBV B cells pulsed with the ORF3P peptide derived from a gene product translated from an alternative open reading of TRP-1/gp75 gene, and the autologous 586mel tumor cells, but did not recognize 586EBV B cells pulsed with an irrelevant peptide. TIL586-C1 was chosen as one representative for these T cell clones as shown in FIG. 1A. However, several T cell clones isolated from the same TIL586 cell line recognized neither 586EBV B cells pulsed with the TRP-1 peptide ORF3P nor COS cells transfected with TRP-1 and HLA-A31 cDNAs, but were capable of recognizing 586mel as well as HLA-A31+ melanocytes (FIG. 1B). These results suggested that these T cell clones recognized additional tumor antigens on the 586mel tumor cells. These T cell clones were then expanded to obtain enough cells for screening cDNA libraries or testing other cDNAs for recognition by methods described in the Materials and Methods section (Example 1). One of clones, CTL clone 4, was successfully expanded and used for further studies as described below.

EXAMPLE 3

Identification of a cDNA Encoding a Tumor Antigen Recognized by T Cell Clones

To determine the HLA molecule responsible for presenting antigen to CTL clone 4, we transfected HLA-A31 cDNA into A31-negative tumor lines such as 397mel and 624mel and tested for recognition by the CTL clone. Transfectants of 397mel and 624mel expressing HLA-A31 were significantly recognized by CTL clone 4 (Table 1). Furthermore, these T cells were also capable of recognizing the HLA-A31 positive allogeneic tumor line 1353mel, indicating that recognition of the tumor antigen by CTL clone 4 was HLA-A31 restricted.

TABLE 1

Specific secretion of GM-CSF by CTL clone 4 is HLA-A31-restricted

| | Stimulators | | |
|---|---|---|---|
| Cell lines | Transfected gene | HLA-A31 expression | GM-CSF secretion (pg/ml) |
| None | none | − | <10 |
| 397mel (TRP1−/TRP2+) | none | none | 23 |
| 397mel (TRP1−/TRP2+) | HLA-A31 | + | 2840 |
| 624mel (TRP1+/1RP2+) | none | − | 39 |
| 624mel (TRP1+/TRP2+) | HLA-A31 | + | 670 |
| 1353mel (TRP1+/TRP2+) | none | + | 879 |
| 586 mel (TRP1+/TRP2+) | none | + | >4000 |
| 586EBVB | none | + | 29 |
| COS-7 | none | − | 35 |
| COS-7 | HLA-A31 | + | 30 |

GM-CSF in the supernatant was measured after 24 h incubation of 2 × 10$_4$ CTL clone 4 cells with either melanoma cell lines or COS-7 transfected with the HLA-A31 cDNA.

Since only a limited number of T cells were available, we first tested whether or not these T cells recognized previously identified tumor antigens or melanocyte-lineage differentiation proteins. Recognition of COS-7 cells transfected with HLA-A31 cDNA and genes encoding the known tumor antigens or putative antigens including MART-1 (Kawakami et al. (1994a)), gp75 (Wang et al. (1995)), gp100 (Kawakami et al. (1994b), tyrosinase (Brichard et al. (1993)), pIS (Robbins et al. (1995)) and TRP-2 (Yokoyama et al. (1994); Bouchard et al. (1994)) by CTL clone 4 was tested. COS cells transfected with HLA-A31 alone or TRP-2 alone did not confer recognition by the T cell clones. However, COS cells transfected with HLA-A31 and TRP-2 cDNA stimulated GM-CSF release from T cells, whereas COS cells transfected with HLA-A31 and other genes did not, indicating that the T cell clone 4 recognized TRP-2 as a tumor antigen in an HLA-A31 restricted manner.

Analysis of the structural similarities in HLA-A3, A11, A31, A33 and A68 and their peptide binding motif has suggested the existence of the A3-like supermotif (Sidney et al. (1996)). A single epitope peptide could cross-react with HLA-A3, A11, A31, A33 and A68 molecules which are cumulatively expressed in about 40–50% of the general population. It has been reported that the same peptide epitope derived from Hepatitis B virus nucleocapsid protein could be presented by HLA-A31 and -A68 molecules and recognized by the corresponding HLA-A31 or -A68 restricted CTL (Missale et al. (1993)). We tested whether HLA-A31 restricted T cells recognized TRP-1 and TRP-2 epitopes when pulsed onto HLA-A3 positive EBV B cells. Interestingly, weak recognition was detected based on GM-CSF release from T cells. However, no recognition of HLA-A3 positive tumor cells was detected.

EXAMPLE 4

Expression of the TRP-2 Gene

Northern blot analyses were performed using TRP-2 cDNA as a probe to evaluate the expression pattern of TRP-2 in different tissues. Normal retinal tissue was shown to be the only positive in the expression of TRP-2 among the normal human tissues tested. The expression pattern of TRP-2 in melanoma cell lines and other cell lines is listed in Table 2 below. Twenty five of thirty melanoma cell lines were found to express TRP-2. The Burkitt's B cell line Daudi and the breast cancer cell line MDA23 1 were negative, in agreement with previous results (Bouchard et al. (1994)). Thus, like tyrosinase, TRP-1, gplOO and MART-1, the expression pattern of this gene appeared to be restricted to melanomas, normal melanocyte cell lines and retina.

TABLE 2

Expression of TRP-2 in different cell lines and human tissues tested

| Melanoma cell lines | Expression of TRP-2 | Cell lines/tissues | Expression of TRP-2 |
|---|---|---|---|
| 397mel | + | A375 | − |
| 526mel | + | 586EBVB | − |
| 397mel | + | Melanocytes | |
| 501mel | + | FM906 | + |
| 537mel | − | FM680 | + |
| 553Bmel | + | Other tumor lines | |
| 586mel | + | Daudi | − |
| 624mel | + | MDA231 | − |
| 677mel | + | Normal tissues | |
| 679mel | − | Retina | + |
| 697mel | + | Testis | − |
| 729mel | − | Brain | − |
| 894mel | + | Spleen | − |
| 836mel | − | Liver | − |
| 888mel | + | Fetal liver | − |
| 928mel | + | Thymus | − |
| 1290mel | + | Lung | − |
| 1300mel | + | | |
| 952mel | + | | |
| HT144mel | + | | |
| 1011mel | + | | |
| 1088mel | + | | |
| SK23 | + | | |

TABLE 2-continued

Expression of TRP-2 in different cell lines and human tissues tested

| Melanoma cell lines | Expression of TRP-2 | Cell lines/tissues | Expression of TRP-2 |
|---|---|---|---|
| SK28 | + | | |
| Maisel | + | | |
| groves | + | | |
| WN266 | + | | |

Expression of TRP-2 was tested by Northern blot analysis with 10–20 ~g of total RNA and probed with the TRP-2 cDNA fragment. Daudi is a Burkitt's B cell line and MDA231 is a breast cancer cell line.

EXAMPLE 5

The Peptide Epitopes Recognized by T Cells

Figure 3:
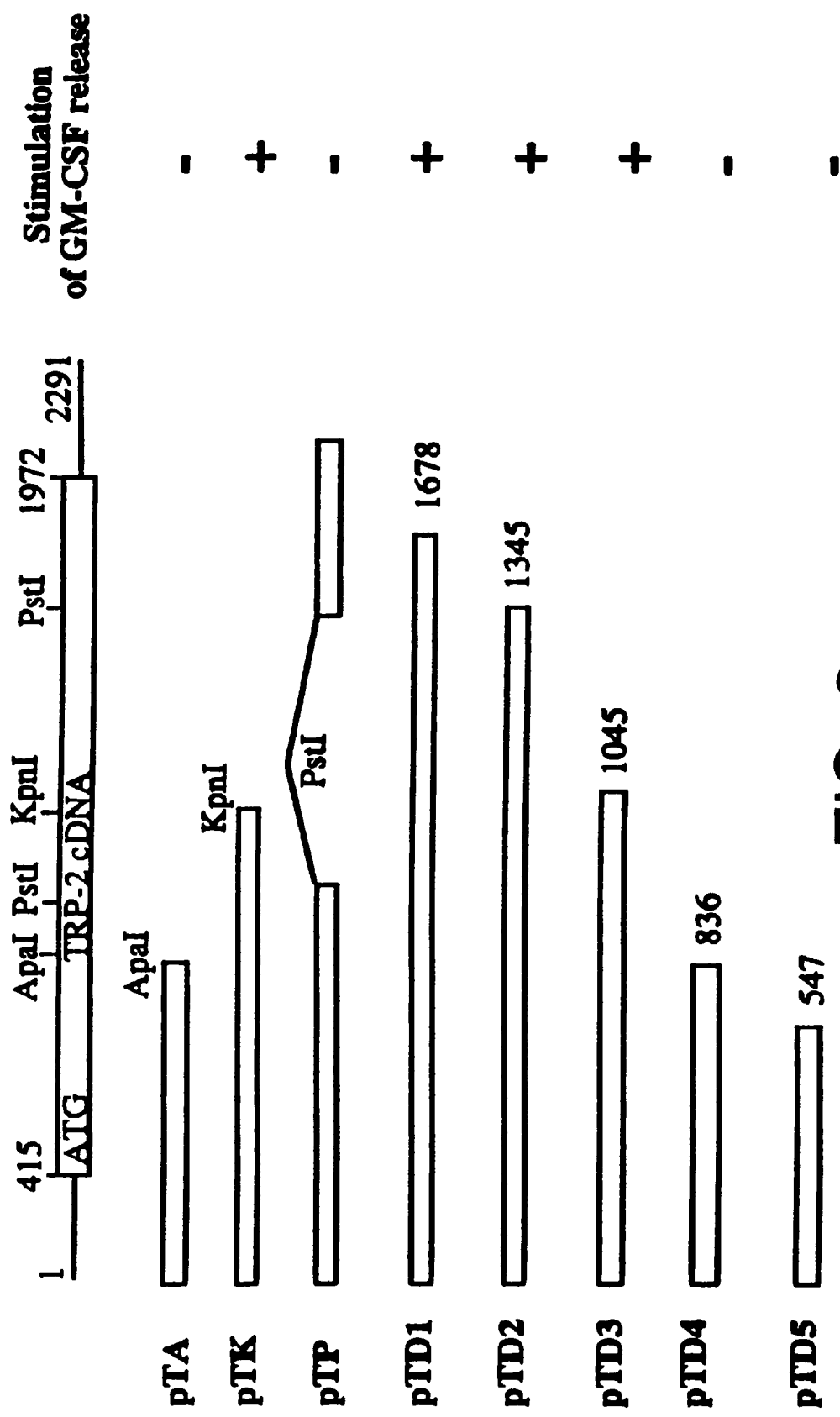
FIG. 3. Construction of deletions and subclones of the TRP-2 gene and T cell recognition. The full length cDNA of TRP-2 which comprises the 1557 bp open reading frame is shown. Nucleotides are numbered from the f~rst nucleotide from the 5' untranslated region of TRP-2 cDNA. A series of deletion constructs and subcloning of DNA fragments were made. T cell recognition of each construct was determined after co-culturing CTL clone 4 with COS-7 co-transfected with the DNA fragments shown above and the HLA-A31 gene.

To determine the antigenic epitopes from TRP-2, a series of nested deletions of the TRP-2 gene from the 3' end using Exo III/S1 nuclease as well as DNA fragments encoding the truncated form of TRP-2 were generated. These deletions and subcloned constructs were transfected into COS-7 cells along with the pBK-CMV plasmid containing the HLA-A31 cDNA. Recognition of the transfected COS cells were tested with CTL clone by measuring GM-CSF cytokine release from the CTL clone. FIG. 3 indicated that pTD1, 2 and 3 constructs retained the ability to stimulate cytokine release from the CTL clone 4, but pTD4 and pTD5 lost the stimulating activity to the CTL clone 4, indicating that the epitope(s) recognized by the CTL clone 4 was located in the region of nucleotides 836–1045. This was consistent with results obtained by the subcloning experiments. Although pTA and pTP lost the ability to stimulate cytokine release from CTL clone 4, pTK still remain positive in the cytokine release assay. Therefore, the epitopes resided in a DNA fragment flanked by the first PstI and KpnI sites as shown in FIG. 4.

To identify the epitopes from the coding region of this small DNA fragment, five synthetic peptides were based on the synthesized peptide binding motif for HLA-A31 (hydrophobic residues at position 2 and positively charged residues at position 9) (Rammensee et al. (1995)). These peptides were pulsed onto 586EBV B cells and tested for their ability to stimulate cytokine release by CTL clone 4. As shown in Table 3, peptide $TRP_{197-205}$ was strongly recognized by CTL clone 4 when pulsed on 586EBV B cells. The recognition of this peptide by CTL clone 4 was observed only when the peptide was pulsed onto HLA-A31+ EBV B cells such as 586EBV and 1510EBV, but not onto HLA-A31 negative T2 cells. CTL clone 4 did not the ORF3P peptide derived from the alternative open reading frame of the TRP-1 gene. These results demonstrated that TIL586-Cl specifically recognized the ORF3P peptide derived from TRP-1 and CTL clone 4 specifically recognized the peptide derived from TRP2. No cross reactivity was observed while both ORF3P and TRP2-p197 were presented to T cells by HLA-A31 molecules.

TABLE 3

Identification of synthetic peptides with reactivity to T cell clones

| Target cells pulsed with peptide | | GM-CSF release | |
|---|---|---|---|
| | | CTL clone 1 (TRP-1) | CTL clone 4 (TRP-2) |
| 586EBV + TRP$_{186-194}$ | VWLHYYSVR(TRP-2) (SEQ ID NO:16) | <50 | <50 |
| 586EBV + TRP$_{185-194}$ | FVWLHYYSVR(TRP-2) (SEQ ID NO:17) | <50 | <50 |
| 586EBV + TRP$_{194-202}$ | RDTLLGPGR(TRP-2) (SEQ ID NO:18) | <50 | <50 |
| 586EBV + TRP$_{197-205}$ | LLGPGRPYR(TRP-2) (SEQ ID NO:4) | <50 | >4000 |
| 586EBV + TRP$_{213-221}$ | GPAFVTWHR(TRP-2) (SEQ ID NO:19) | <50 | <50 |
| 586EBV + ORF3P | MSLQRQFLR(TRP-1) (SEQ ID NO;20) | >8000 | <50 |
| 1510EBV + TRP$_{197-205}$ | LLGPGRPYR(TRP-2) (SEQ ID NO:4) | <50 | >4000 |
| 1510EBV + ORF3P | MSLQRQFLR(TRP-1) (SEQ ID NO:20) | >6000 | <50 |
| T2 + TRP$_{197-205}$ | LLGPGRPYR(TRP-2) (SEQ ID NO:4) | <50 | <50 |
| T2 + ORF3P | MSLQRQFLR(TRP-1) (SEQ ID NO:20) | <50 | <50 |
| 586EBV + None | | <50 | <50 |
| 586EBV + None | | >5000 | >3000 |

586EBV cells were incubated with individual peptides at a concentration of 1~g/ml for 90 min.
GM-CSF release was measured after co-incubation of peptide-loaded 586EBV cells with T cell clones recognizing either TRP-1 or TRP-2. GM-CSF secretion by T cells alone without stimulators was subtracted. 586EBV and 1510EBV were EBV transformed B cell lines expressing HLA-A3 1.

EXAMPLE 6

Characterization of TRP$_{197-205}$ Peptide

Figure 5C:
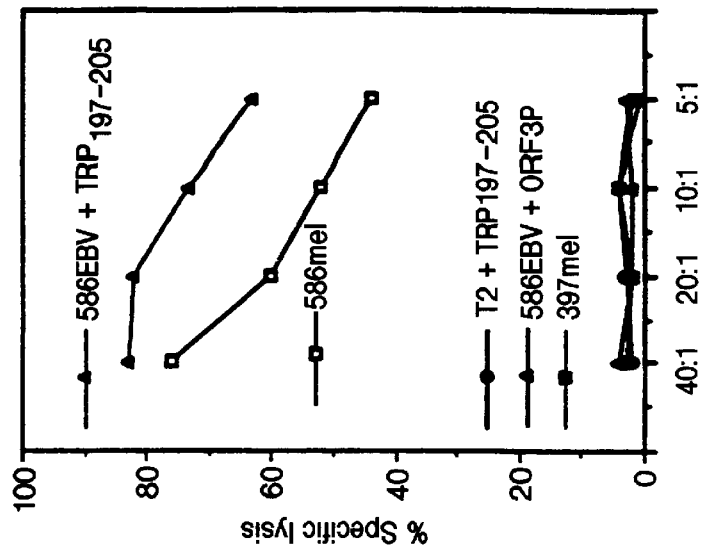
FIGS. 5A–C. Characterization of the Antigenic peptide recognized by CTL clone 4. (5A). GM-CSF release by T cells at different peptide concentrations. 586EBV (A31+) were pulsed with the $TRP_{197-205}$ peptide (—▲—) and T2 (non-A31) cells were pulsed with the $TRP_{197-205}$ (—●—) at various peptide concentrations for 90 min. ORF3P as a control peptide was pulsed onto 586EBV B cells (--Δ--). GM-CSF release by CTL clone 4 was determined after co-incubate with 586EBV B cells pulsed with $TRP_{197-205}$ and ORF3P, and T2 cells pulsed with $TRP_{197-205}$.
Figure 5B:
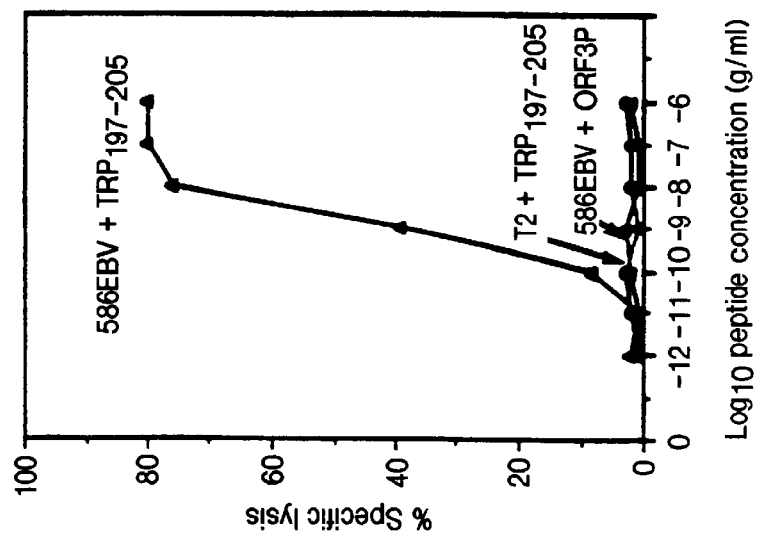
Figure 5A:
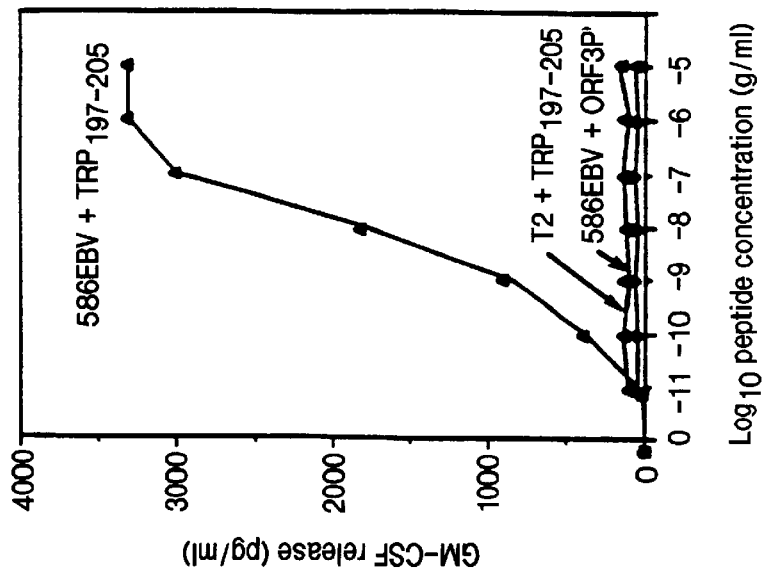

Titration experiments demonstrated that 1 nM of peptide was sufficient to stimulate GM-CSF release from the T cell clone 4 and the stimulation reached a plateau at 500 nM (FIG. 5A). Lysis of 586EBV B cells pulsed with TRP$_{197-205}$ by CTL clone 4 was also determined at various peptide concentrations (FIG. 5B), and similar to cytokine release assays, lysis of target cells by the CTL clone 4 was detected at 1 nM peptide concentration. Maximum lysis was seen at 100 nM of peptide concentration. CTL clone 4 was capable of lysing 586EBV pulsed with TRP2-p197 and 586mel tumor cells even at low E:T ratio, but failed to lyse 586EBV B cells alone or pulsed with the control peptide ORF3P nor the HLA-A31 negative 397mel line (FIG. 5C).

The majority of human melanoma antigens identified to date are non-mutated self-antigens and the T cell recognition and binding affinity of these self-peptides to the corresponding MHC molecules has in some instances been improved by substitution of amino acids at anchor residues (Parkburst et al. (1996)). A number of synthetic peptides including 8mer or 10mer and modified peptides as indicated in Table 4 were made and tested for recognition by CTL clone 4 when pulsed onto 586EBV B cells. The 1omer TLLGPGRPYR (SEQ ID NO:5), in which one amino acid was extended at the N-terminus of TRP$_{197-205}$, was still recognized by CTL clone 4 when pulsed on 586EBV B cells, but the reactivity was about 60% of the overlapping 9mer LLGPGRPYR (SEQ ID NO:4). Based on the binding motif of HLA-A31, a few modified peptides were generated with substitution of amino acids at anchor residues positions 2 and 9 as well as at other positions. The Arg residue at position 9 in the C-terminus could be substituted with the Lys residue and the modified peptide retained at least 60% of the activity of the parental peptide. Substitution of a Leu residue at position 2 with either Ser, Ile or Val residues retained the same activity or reduced the activity to 60% of the parental peptide while substitution with Ala or Phe at this position reduced the ability to stimulate cytokine release from T cells (Table 4). Other modifications provided variable cancer peptide activity in T cell recognition.

TABLE 4

Comparison of T cell reactivity of modified peptides

| Target cells pulsed with peptides | CTL clone 4 GM-CSF release |
|---|---|
| 586EBV + LLGPGRPYR (SEQ ID NO:4) | 3450 |
| 586EBV + TLLGPGRPYR (SEQ ID NO:5) | 2100 |
| 586EBV + LLGPGRPYRA (SEQ ID NO:6) | 545 |
| 586EBV + LGPGRPYR (SEQ ID NO:4 amino acids 2–9) | <50 |
| 586EBV + LIGPGRPYR (SEQ ID NO:7) | 2545 |
| 586EBV + LVGPGRPYR (SEQ ID NO:4) | 2100 |
| 586EBV + LSGPGRPYR (SEQ ID NO:9) | 3300 |
| 586EBV + LAGPGRPYR (SEQ ID NO:10) | 550 |
| 586EBV + LFGPGRPYR (SEQ ID NO:21) | <50 |
| 586EBV + LLGPGRPYK (SEQ ID NO:11) | 2000 |
| 586EBV + LLGPGRPYH (SEQ ID NO:22) | <50 |
| 586EBV + ALGPGRPYR (SEQ ID NO:23) | <50 |
| 586EBV + RLGPGRPYR (SEQ ID NO:24) | <50 |
| 586EBV + KLGPGRPYR (SEQ ID NO:12) | 420 |
| 586EBV + LLLPGRPYR (SEQ ID NO:25) | <50 |
| 586EBV + LLFPGRPYR (SEQ ID NO:26) | <50 |
| 586EBV + LLAPGRPYR (SEQ ID NO:27) | <50 |
| 586EBV + LLGPGFPYR (SEQ ID NO:13) | 738 |
| 586EBV + LLGPGAPYR (SEQ ID NO:28) | <50 |
| 586EBV + LLGPGIPYR (SEQ ID NO:29) | <50 |
| 586EBV + LLGPGVPYR (SEQ ID NO:30) | <50 |
| 586EBV + LLGPGKPYR (SEQ ID NO:14) | 321 |
| 586EBV | <50 |
| 586mel | >3000 |

586EBV cells were incubated with individual peptides at a concentration of 0.5 ~g/ml for 90 min. GM-CSF release was measured after co-incubation of peptide-loaded 586EBV cells with the CTL clone 4 cells. GM-CSF secretion by T cells alone without stimulators was subtracted. 586EBV was a EBV transformed B cell line expressing HLA-A31.

The TRP-2 protein contains two putative copper-binding sites, cysteine-rich regions and a transmembrane domain. Human TRP-2 has been mapped to chromosome 13 while the mouse counterpart has been mapped to chromosome 14 in the region of the coat color mutation, slaty. There is about a 40% amino acid sequence identity between TRP-2 and tyrosinase or TRP-1/gp75, but no CTL line or clone was found thus far that recognizes a common peptide epitope among the tyrosinase protein family.

The 9 mer TRP$_{197-205}$ peptide recognized by CTL clone 4 is located at one of the copper binding sites in the coding region of TRP-2. This peptide most efficiently stimulated cytokine release from T cells compared with other peptides including motified peptides tested in this study. This was in agreement with the predicted HLA-A31 binding motif, which indicates that Leu at position 2 and Arg at position 9 are the favorable residues. Although Leu at position 2 and Arg at position 9 could be replaced with Ile and Ser at position 2 and Lys at position 9, respectively, with little or minor loss of reactivity to T cell recognition, substitutions of amino acids at positions 1, 3 or 6 led to some loss of reactivity.

EXAMPLE 7

In vivo Treatment Assay

For in vivo treatment, MHL-A31$^+$transgenic mice are challenged with either $1 \times 10^5$ or $5 \times 10^5$ Trp-1$^+$ B16 mouse melanoma cells intravenously in order to establish pulmonary metastases. Mice are subsequently vaccinated with a recombinant virus expressing cancer peptide, LLGPGRPYR (SEQ ID NO:4) at $10^5$ PFU/mg body weight. Mice are euthanized on day 12 and the number of pulmonary metastases in vaccinated mice vs. non-vaccinated mice determined.

EXAMPLE 8

Cancer Antigen Specific T Lymphocytes Immunotherapy

T-lymphocytes presensitized to a melanoma antigen may be effective in therapeutically treating mammals afflicted with a melanoma. T-lymphocytes are isolated from peripheral blood or melanoma tumor suspensions and cultured in vitro (Kawakami et al (1988)).

The T lymphocytes are exposed to the cancer peptide, LLGPGRPYR (SEQ ID NO:4) at a concentration of 1 μg/ml alone or in the presence of IL-2, resensitized and expanded in culture. T-lymphocytes exposed to the cancer peptide are administered to a mammal at about $10^9$ to $10^{12}$ lymphocytes per mammal. The lymphocytes are administered either intravenously, intraperitoneally or intralesionally. The treatment may be administered concurrently with other therapeutic treatments such as cytokines, surgical excision of melanoma lesions and chemotherapeutic drugs.

EXAMPLE 9

Treatment of Patients with Metastatic Melanoma

In this protocol, patients with advanced melanoma are immunized with an antigenic cancer epitope.

Patients eligible for the trial must have evidence of measurable or evaluable metastatic melanoma that has failed standard effective therapy. Patients must have tumors that express the TPI-2 antigen as evidenced by PCR or Northern Blot analysis of tumor cell RNA.

Patients receive either 1 ng, 1 μg, 1 mg or 500 mg/kg body weight of a cancer peptide LLGPGRPYR (SEQ ID NO:4) via intravenously at day zero, day 7 and day 14 alone or in combination with IL-2 and/or a co-immunostimulatory molecule. Patients are evaluated for toxicity, immunologic effects and therapeutic efficacy.

Lymphocytes taken from the treated patients are tested for specific response to the cancer antigen comprising the amino acid sequence LLGPGRPYR (SEQ ID NO:4).

A complete response is defined as the disappearance of all clinical evidence of disease that lasts at least four weeks. A partial response is a 50% or greater decrease in the sum of the products of the perpendicular diameter of all measurable lesions for at least four weeks with no appearance of new lesions or increase in any lesions. Minor responses are defined as 25–49% decrease in the sum of the products of the perpendicular diameters of all measurable lesions with no appearance of new lesions and no increase in any lesions. Any patient with less than a partial response is considered a non-responder. The appearance of new lesions or greater than 25% increase in the product of perpendicular diameters of prior lesions following a partial or complete response is considered as a relapse.

References

1. Acsadi, G., G. Dickson, D. R. Love, A. Jani, F. S. Walsh, A. Gurusinghe, J. A. Wolff, and K. E. Davies, 1991, *Nature* 352:815.

2. Ausubel et al., 1987, in Current Protocols in Molecular Biology, John Wiley and Sons, New York, N.Y.

3. Baxby and Paoletti, 1992, *Vaccine* 10:8–9.

4. Bodansky, M. et al. "Peptide Synthesis," John Wiley & Sons Second Edition, 1976.

5. Boel, P., C. Wildmann, M. L. Sensi, R. Brasseur, J. C. Renauld, P. Coulie, T. Boon, and P. Van der Bruggen, 1995, *Immunity.* 2:167–175.

6. Boon, T., J.-C. Cerottini, B. Van Den Eynde, P. Van der Bruggen, and A. Van Pel, 1994, *Annul Rev. Immunol.* 12:337–365.

7. Bouchard, B., V. Del Marmol, I. J. Jackson, D. Cherif, and L. Dubertret, 1994, *Eur. J. Biochem.* 219:127–134.

8. Brichard, V., A. Van Pel, T. Wolfel, C. Wolfel, E. De Plaen, B. Lethe, P. Coulie, and T. Boon, 1993, *J Exp. Med.* 178:489–495.

9. Campbell et al., 1964, "Methods and Immunology", W. A. Benjamin, Inc.

10. Campbell, (1985), "Monoclonal Antibody Technology, the Production and Characterization of Rodent and Human Hybridomas" in Burdon et al. (eds.) "Laboratory Techniques in Biochemistry and Molecular Biology", Vol. 13, Elsevier Science Publishers, Amsterdam).

11. Cooney, E. L., A. C. Collier, P. D. Greenberg, R. W. Coombs, J. Zarling, D. E. Arditti, M. C. Hoffman, S. L. Hu and L. Correy, 1991, Lancet 337:567.

12. Coulie, P. G., V. Brichard, A. Van Pel, T. Wolfel, J. Schneider, C. Traversari, S. Mattei, E. D. De Plaen, C. L. urquin, J.-P. Szikora, J.-C. Reauld, and T. Boon, 1994, *J. Exp. Med.* 180:35–42.

13. Coulie, P. G., F. Lehmann, B. Lethe, J. Herman, C. Lurquin, M. Andrawiss, and T. Boon, 1995, *Proc. Natl. Acad. Sci. U. S. A.* 92:7976–7980.

14. Davis, H. L., R. G. Whalen, and B. A. Demeniex, 1993, *Hum. Gene Ther.* 4:151.

15. Eisenbraum, M. D., D. H. Fuller, and J. R. Haynes, 1993, *DNA and Cell Bio.* 12:791.

16. Fuller, D. H. and J. R. Haynes, 1994, *AIDS Res. Hum. Retrovir.* 10(11):1433.

17. Fynan, E. R., Webster, D. H. Fuller, J. R. Haynes, J. C. Santoro, and H. L. Robinson, 1995, *Proc. Natl. Acad. Sci. USA* 90:11478.

18. Gaugler, B., B. Van Den Eynde, P. Van der Bruggen, P. Romero, J. J. Gaforio, E. De Plaen, B. Lethe, F. Brasseur, and T. Boon, 1994, *J. Exp. Med.* 179:921–930.

19. Gellerich, 1984, "Methods in Immunodiagnosis", 2nd Edition.

20. Harlow and Lane (eds), 1988, In "Antibodies A Laboratory Manual", Cold Spring Harbor Press, Cold Spring Harbor, N.Y.

21. Harrison, G. S. et al., 1995, *Bio Techniques* 19:816–823.

22. Huse et al., 1989, *Science* 246:1275–1281.

23. Houghton, A. N., 1994, *J. Exp. Med.* 180:1–4.

24. Kaufman et al., 1991. *Int. J. Cancer* 48:900–907.

25. Kawakami, Y. et al., 1988, *J. Exp. Med.* 168:2183–2191.

26. Kawakami, Y., S. Eliyahu, C. H. Delgaldo, P. F. Robbins, L. Rivoltini, S. L. Topalian, T. Miki, and S. A. Rosenberg, 1994a, *Proc. Natl. Acad. Sci. U. S. A.* 91:3515–3519.

27. Kawakami, Y., S. Eliyabu, C. H. Delgado, P. F. Robbins, K. Sakaguchi, E. Appella, J. R. Yannelli, G. J. Adema, T. Miki, and S. A. Rosenberg, 1994b, *Proc. Natl. Acad. Sci. USA* 91:6458–6462.

28. Kohler and Milstein, 1975, *Nature* 256, 495–497.

29. Meienhofer, J., 1983, "Hormonal Proteins and Peptides" Vol. 2 p. 46, Academic Press, New York.

30. Missale, G., A. Redeker, J. Person, P. Fowler, S. Guilhot, H. J. Schlicht, C. Ferrari, and F. V. Chisari, 1993, *J. Exp. Med.* 177:751–762.

31. Moss, 1991, *Science* 252:1662.

32. Nabel, E. G. et al., 1992a, *Hum. Gene. Ther.* 3:367–275.

33. Nabel, G. J. et al., 1992b, *Hum. Gene Ther.* 3:649–656.

34. Nabel, G. J. et al., 1993, *Proc. Natl. Acad. Sci. USA* 90:11307–11311.

35. Oellerich, M., 1984, *J. Clin. Chem. Clin. Biochem.* 22:895–904.

36. Pardoll, D. M., 1994, *Nature* 369:357358.

37. Parkburst, M. R., M. Salgaller, S. Southwood, P. Robbins, A. Sette, S. A. Rosenberg, and Y. Kawakami, 1996, *J. Immunol.* In press.

38. Perkus et al., 1985, Science 229:981–984.

39. Rammensee, H. G., T. Friede, and S. Stevanoviic, 1995, *Immunogenetics.* 41:178–228.

40. Robbins, P. F., M. El-Gamil, Y. Kawakami, E. Stevens, J. Yannelli, and S. A. Rosenberg, 1994, *Cancer Research* 54:3124–3126.

41. Robbins, P. F., M. El-Gamil, Y. F. Li;S. L. Topalian, L. Rivoltini, K. Sakaguchi, E. Appella, Y. Kawakami, and S. A. Rosenberg, 1995, *J. Immunol.* 154:5944–5950.

42. Robbins, P. F., M. El-Gamil, Y. F. Li, Y. Kawakami, D. Loftus, E. Appella, and S. A. Rosenberg, 1996, *J. Exp. Med.* 183:1185–1192.

43. Rose and Bigazzi, eds. John Wiley & Sons, 1980.

44. Rosenberg, S. A., B. S. Packard, P. M. Aebersold, D. Solomon, S. L. Topalian, S. T. Toy, P. Simon, M. T. Lotze, J. C. Yang, C. A. Seipp, C. Simpson, C. Carter, S. Bock, D. Schwartzentruber, J. P. Wei, and D. E. White, 1988, *N. Engl. J. Med.* 319:1676–1680.

45. Rosenberg, S. A., J. Y. Yannelli, and J. C. Yang, 1994, *J. Natl. Cancer Inst.* 86:1159–1166.

46. Rosenberg, S., 1995, *The Cancer Journal* 1:90–100.

47. Sambrook et al., 1989, in: "Molecular Cloning A Laboratory Manual", Cold Spring Harbor press, Plainview, N.Y.

48. Schroder, E., Kubbe, K., 1965, "The Peptides" Vol. 1, Academic Press, New York.

49. Sidney, J., H. M. Grey, S. Southwood, E. Celis, P. A. Wentworth, M. F. del Guercio, R. Kubo, R. W. Chesnut, and A. Sette, 1996, *Human Immunol.* 45:79–93.

50. Smith and Moss, 1984, *BioTechniques* November/December, p. 306–312.

51. Steward, J. M., Young, J. D., 1969, "Solid Phase Peptide Synthesis", W. H. Freeman & Co., San Francisco.

52. Stewart, M. J. et al., 1992, *Hum. Gene Ther.* 3:399–410.

53. Sutter and Moss, 1992, *Proc. Nat'l Acad. Sci. U.S.A.* 89:10847–10851.

54. Topalian, S., D. Solomon, F. P. Avis, A. E. Chang, D. L. Freeksen, W. M. Linehan, M. T. Lotze, C. N. Robertson, C. A. Seipp, P. Simon, C. G. Simpson, and S. A. Rosenberg, 1988, *J. Clin. Oncol.* 6:839–853.

55. Tsomides, T. J. and H. N. Eisen, 1994, *Proc. Natl. Acad. Sci. USA* 91:3487–3489.

56. Van Den Eynde, B., O. Peeters, O. De Backer, B. Gaugler, S. Lucas, and T. Boon, 1995, *J. Exp. Med.* 182:689–698.

57. Van der Bruggen, P., C. Traversari, P. Chomez, C. Lurquin, E. DePlaen, B. Van Den Eynde, A. Knuth, and T. Boon, 1991, *Science* 254: 1643–1647.

58. Walter, E. A., P. D. Greenberg, M. J. Gibert, R. J. Finch, K. S. Watanabe, E. D. Thomas, and S. R. Riddell, 1995, *N. Engl. J. Med.* 333:1038–1044.

59. Wang, R. F, P. F. Robbins, Y. Kawakami, X. Q. Kang, and S. A. Rosenberg, 1995, *J. Exp. Med.* 181:799–804.

60. Wang, R. and S. A. Rosenberg, 1996a, *J. Leukocyte Biol.* In press.

61. Wang, R. F., M. R. Parkhurst, Y. Kawakami, P. F. Robbins, and S. A. Rosenberg, 1996b, *J. Exp. Med.* 183:1131–1140.

62. Williams, R. S., S. A. Johnston, M. Riedy, M. J. DeVit, S. G. McElligott, and J. C. Sanford, 1991, *Proc. Natl. Acad. Sci. USA* 88:2726.

63. Wolfe, T., M. Hauer, J. Schneider, M. Serrano, C. Wolfel, E. Klehmann-Hieb, E. De Plaen, T. Hankeln, K. H. Meyer Zum Buschenfelde, and D. Beach, 1995, *Science* 269:1281–1284.

64. Wolff, J. A., R. W. Malone, P. Williams, W. Chong, G. Acsadi, A. Jani, and P. L. Felgner, 1990, *Science* 247:1465.

65. Yang, N. S., J. Burkholder, B. Roberts, B. Martinelli, and D. McCabe, 1990, *Proc. Natl. Acad. Sci. USA* 87:9568.

66. Yokoyama, K., H. Suzuki, K-I. Yasumoto, Y. Tomita, and S. Shibahara, 1994, *Biochim. Biophys. Acta* 1217:317–321.

We claim:

1. An isolated nucleic acid which is a fragment of SEQ ID NO:1 and which encodes a tumor antigen wherein said tumor antigen stimulates cancer antigen specific T lymphocytes.

2. An isolated nucleic acid sequence according to claim 1 wherein the nucleic acid sequence is derived from a cancer selected from the group consisting of melanoma metastases and melanoma.

3. An isolated nucleic acid sequence according to claim 1 wherein the nucleic acid sequence comprises TTATTAG-GACCAGGACGCCCCTACAGG (SEQ ID NO:15) or a portion or variant thereof, wherein said antigen stimulates cancer antigen specific T lymphocytes.

4. A recombinant virus comprising a viral genome or portion thereof which has incorporated therein the nucleic acid sequence according to claim 1.

5. The isolated nucleic acid of claim 1 wherein said fragment is nucleotides 1–1678 of SEQ ID NO:1.

6. The isolated nucleic acid of claim 1 wherein said fragment is nucleotides 1–1345 of SEQ ID NO:1.

7. The isolated nucleic acid of claim 1 wherein said fragment is nucleotides 1–1045 of SEQ ID NO:1.

8. The isolated nucleic acid of claim 1 wherein said fragment is nucleotides 836–1045 of SEQ ID NO:1.

9. An isolated nucleic acid sequence according to claim 2 wherein the sequence encodes an amino acid sequence:

$X^1$LLGPGRPYR$X^2$ (SEQ ID NO:3) and variants thereof, wherein $X^1$ and $X^2$ are identical or different and each are one or more amino acids.

10. A recombinant expression vector comprising the nucleic acid sequence according to claim 3.

11. An oligonucleotide comprising a nucleic acid sequence complementary to the nucleic acid sequence according to claim 3.

12. A recombinant virus according to claim 4 further comprising at least one gene encoding a co-immunostimulatory molecule.

13. The recombinant virus according to claim 4 wherein the virus is selected from the group consisting of retrovirus, baculovirus, Ankara virus, fowlpox virus, adenovirus, and vaccinia virus.

14. The recombinant virus according to claim 4 wherein the tumor antigen is derived from melanocytes.

15. A host cell transformed or transfected with a recombinant expression vector according to claim 10.

16. A recombinant virus according to claim 12 wherein the co-immunostimulatory molecule is a MHC class I molecule.

17. A recombinant virus according to claim 12 wherein the nucleic acid sequence comprises:

TTATTAGGACCAGGACGCCCCTACAGG (SEQ ID NO:15).

18. A recombinant virus according to claim 12 wherein the nucleic acid sequence encodes a tumor antigen comprising the amino acid sequence:

$X^1$LLGPGRPYR$X^2$ (SEQ ID NO:3), or a variant thereof wherein $X^1$ and $X^2$ are identical or different and each are one or more amino acids.

19. A method of producing a recombinant TRP-2 tumor antigen comprising:

a. inserting a nucleotide sequence consisting of a portion of SEQ ID NO:1, or variant thereof, which encodes a tumor antigen that stimulates cancer antigen specific T lymphocytes into an expression vector;

b. transferring the expression vector into a host cell;

c. culturing the host cell under conditions appropriate for expression of the tumor antigen; and d. harvesting the recombinant tumor antigen.

20. A method according to claim 19 further comprising in step (a) inserting a nucleotide sequence encoding an MHC class I molecule into the expression vector.

21. A method of detecting the presence of cancer or precancer in a mammal comprising:

contacting a nucleic acid sequence comprising a hybridizing portion of SEQ ID NO:1 or a variant thereof with a test biological sample of mRNA taken from the mammal under high stringency hybridization conditions allowing for a complex to form between the sequence and the mRNA; and detecting the complex, presence of said complex being indicative of the presence of cancer or precancer, wherein the cancer or precancer is melanoma.

22. An isolated nucleic acid encoding a tumor antigen, wherein said antigen consists of an amino acid sequence which is a fragment of SEQ ID NO:2 or a variant thereof wherein said fragment or variant thereof stimulates cancer antigen specific T lymphocytes.

23. The nucleic acid according to claim 22, wherein said antigen is a cancer peptide, immunologically recognized by MHC restricted T lymphocytes.

24. The nucleic acid according to claim 22, wherein said antigen comprises SEQ ID NO:4 a variant thereof.

25. The nucleic acid according to claim 22, wherein the antigen comprises the amino acids sequence: Leu Xaa Gly Pro Gly Arg Pro Tyr Xaa (SEQ ID NO:31) wherein the first Xaa is selected from the group consisting of Ile, Ser, Leu and Val;

and the second Xaa is selected form the group consisting of Lys and Arg.

26. The nucleic acid according to claim 23, wherein the T lymphocytes are HLA-A31 restricted.

27. An isolated nucleic acid encoding a tumor antigen, wherein said antigen consists of an amino acid sequence which is a fragment of SEQ ID NO:2 or a variant thereof wherein said fragment or variant thereof stimulates cancer antigen specific T lymphocytes, wherein the tumor antigen is a cancer peptide selected from the group consisting of SEQ ID NO:4 through SEQ ID NO:14.

* * * * *

SEQUENCE LISTING (1) GENERAL INFORMATION:

(iii) NUMBER OF SEQUENCES: 31

(2) INFORMATION FOR SEQ ID NO:1:

(i) SEQUENCE CHARACTERISTICS:
      (A) LENGTH: 2291
      (B) TYPE: NUCLEIC ACID
      (C) STRANDEDNESS: DOUBLE
      (D) TOPOLOGY: UNKNOWN (ii) MOLECULE TYPE:
      (A) DESCRIPTION: cDNA (ix) FEATURE:
      (A) NAME/KEY: TRP-2 GENE
      (B) LOCATION:
      (C) IDENTIFICATION METHOD:
      (D) OTHER INFORMATION:

(x) PUBLICATION INFORMATION:
      (A) AUTHORS: YOKAYAMA, ET AL.
      (B) TITLE: MOLECULAR CLONING AND FUNCTIONAL
          ANALYSIS OF A cDNA CODING FOR HUMAN
          DOPACHROME TAUTOMERASE/TYROSINASE-RELATED
          PROTEIN-2.
      (C) JOURNAL: BIOCHIM. BIOPHSY. ACTA.
      (D) VOLUME: 1217
      (E) ISSUE:
      (F) PAGES: 317-321
      (G) DATE: 1994

(xi) SEQUENCE DESCRIPTION:SEQ ID NO:1:

```
GCAATTAAAG TCAAGAGCTA AGGAGGGAGG GAGAGGGTTT                40

AGAAATACCA GCATAATAAG TAGTATGACT GGGTGCTCTG                80

TAAATTAACT CAATTAGACA AAGCCTGACT TAACGGGGGA               120

AGATGGTGAG AAGCGCTACC CTCATTAAAT TTGGTTGTTA               160

GAGGCGCTTC TAAGGAAATT AAGTCTGTTA GTTGTTTGAA               200

TCACATAAAA TTGTGTGTGC ACGTTCATGT ACACATGTGC               240

ACACATGTAA CCTCTGTGAT TCTTGTGGGT ATTTTTTTAA               280

GAAGAAAGGA ATAGAAAGCA AAGAAAAATA AAAAATACTG               320

AAAAGAAAAG ACTGAAAGAG TAGAAGATAA GGAGAAAAGT               360

ACGACAGAGA CAAGGAAAGT AAGAGAGAGA GAGAGCTCTC               400

CCAATTATAA AGCCATGAGC CCCCTTTGGT GGGGGTTTCT               440

GCTCAGTTGC TTGGGCTGCA AAATCCTGCC AGGAGCCCAG               480

GGTCAGTTCC CCCGAGTCTG CATGACGGTG GACAGCCTAG               520

TGAACAAGGA GTGCTGCCCA CGCCTGGGTG CAGAGTCGGC               560

CAATGTCTGT GGCTCTCAGC AAGGCCGGGG GCAGTGCACA               600

GAGGTGCGAG CCGACACAAG GCCCTGGAGT GGTCCCTACA               640

TCCTACGAAA CCAGGATGAC CGTGAGCTGT GGCCAAGAAA               680

ATTCTTCCAC CGGACCTGCA AGTGCACAGG AAACTTTGCC               720

GGCTATAATT GTGGAGACTG CAAGTTTGGC TGGACCGGTC               760

CCAACTGCGA GCGGAAGAAA CCACCAGTGA TTCGGCAGAA               800
```

```
CATCCATTCC TTGAGTCCTC AGGAAAGAGA GCAGTTCTTG           840

GGCGCCTTAG ATCTCGCGAA GAAGAGAGTA CACCCCGACT           880

ACGTGATCAC CACACAACAC TGGCTGGGCC TGCTTGGGCC           920

CAATGGAACC CAGCCGCAGT TTGCCAACTG CAGTGTTTAT           960

GATTTTTTTG TGTGGCTCCA TTATTATTCT GTTAGAGATA          1000

CATTATTAGG ACCAGGACGC CCCTACAGGG CCATAGATTT          1040

CTCACATCAA GGACCTGCAT TTGTTACCTG GCACCGGTAC          1080

CATTTGTTGT GTCTGGAAAG AGATCTCCAG CGACTCATTG          1120

GCAATGAGTC TTTTGCTTTG CCCTACTGGA ACTTTGCCAC          1160

TGGGAGGAAC GAGTGTGATG TGTGTACAGA CCAGCTGTTT          1200

GGGGCAGCGA GACCAGACGA TCCGACTCTG ATTAGTCGGA          1240

ACTCAAGATT CTCCAGCTGG GAAACTGTCT GTGATAGCTT          1280

GGATGACTAC AACCACCTGG TCACCTTGTG CAATGGAACC          1320

TATGAAGGTT TGCTGAGAAG AAATCAAATG GGAAGAAACA          1360

GCATGAAATT GCCAACCTTA AAAGACATAC GAGATTGCCT          1400

GTCTCTCCAG AAGTTTGACA ATCCTCCCTT CTTCCAGAAC          1440

TCTACCTTCA GTTTCAGGAA TGCTTTGGAA GGGTTTGATA          1480

AAGCAGATGG GACTCTGGAT TCTCAAGTGA TGAGCCTTCA          1520

TAATTTGGTT CATTCCTTCC TGAACGGGAC AAACGCTTTG          1560

CCACATTCAG CCGCCAATGA TCCCATTTTT GTGGTTCTTC          1600

ATTCCTTTAC TGATGCCATC TTTGATGAGT GGATGAAAAG          1640

ATTTAATCCT CCTGCAGATG CCTGGCCTCA GGAGCTGGCC          1680

CCTATTGGTC ACAATCGGAT GTACAACATG GTTCCTTTCT          1720

TCCCTCCAGT GACTAATGAA GAACTCTTTT TAACCTCAGA          1760

CCAACTTGGC TACAGCTATG CCATCGATCT GCCAGTTTCA          1800

GTTGAAGAAA CTCCAGGTTG GCCCACAACT CTCTTAGTAG          1840

TCATGGGAAC ACTGGTGGCT TTGGTTGGTC TTTTTGTGCT          1880

GTTGGCTTTT CTTCAATATA GAAGACTTCG AAAAGGATAT          1920

ACACCCCTAA TGGAGACACA TTTAAGCAGC AAGAGATACA          1960

CAGAAGAAGC CTAGGGTGCT CATGCCTTAC CTAAGAGAAG          2000

AGGCTGGCCA AGCACAGTT CTGACGCTGA CAATAAAGGA          2040

ACTAATCCTC ACTGTTCCTT CTTGAGTTGA AGATCTTTGA          2080

CATAGGTTCT TCTATAGTGA TGATGATCTC ATTCAGAAGA          2120

TGCTTAGCTG TAGTTTCCGC TTTGCTTGCT TGTTTAACAA          2160

ACCCAACTAA AGTGCTTGAG GCTACCTCTA CCTTCAAATA          2200

AAGATAGACC TGACAATTTG TGATATCTAA TAATAACCCC          2240

CCCCCCAATA TTGATTAAGC CTCCTCCTTT TCTGAAAGCA          2280

TTTAAAAAAA A                                        2291
```

(2) INFORMATION FOR SEQ ID NO:2:

(i) SEQUENCE CHARACTERISTICS:
        (A) LENGTH: 519
        (B) TYPE: AMINO ACID
        (C) STRANDEDNESS: SINGLE
        (D) TOPOLOGY: UNKNOWN (ii) MOLECULE TYPE:
        (A) DESCRIPTION: PROTEIN (ix) FEATURE:
        (A) NAME/KEY: TRP-2 PROTEIN
        (B) LOCATION:
        (C) IDENTIFICATION METHOD:
        (D) OTHER INFORMATION:

(x) PUBLICATION INFORMATION:
        (A) AUTHORS: YOKAYAMA, ET AL.
        (B) TITLE: MOLECULAR CLONING AND FUNCTIONAL
            ANALYSIS OF A cDNA CODING FOR HUMAN
            DOPACHROME TAUTOMERASE/TYROSINASE-RELATED
            PROTEIN-2.
        (C) JOURNAL: BIOCHIM. BIOPHSY. ACTA.
        (D) VOLUME: 1217
        (E) ISSUE:
        (F) PAGES: 317-321
        (G) DATE: 1994

(xi) SEQUENCE DESCRIPTION:SEQ ID NO:2:

```
Met Ser Pro Leu Trp Trp Gly Phe Leu Leu Ser Cys
1               5                   10

Leu Gly Cys Lys Ile Leu Pro Gly Ala Gln Gly Gln
            15                  20

Phe Pro Arg Val Cys Met Thr Val Asp Ser Leu Val
25                  30                  35

Asn Lys Glu Cys Cys Pro Arg Leu Gly Ala Glu Ser
                40                  45

Ala Asn Val Cys Gly Ser Gln Gln Gly Arg Gly Gln
        50                  55                  60

Cys Thr Glu Val Arg Ala Asp Thr Arg Pro Trp Ser
                65                  70

Gly Pro Tyr Ile Leu Arg Asn Gln Asp Asp Arg Glu
            75                  80

Leu Trp Pro Arg Lys Phe Phe His Arg Thr Cys Lys
85                  90                  95

Cys Thr Gly Asn Phe Ala Gly Tyr Asn Cys Gly Asp
                100                 105

Cys Lys Phe Gly Trp Thr Gly Pro Asn Cys Glu Arg
        110                 115                 120

Lys Lys Pro Pro Val Ile Arg Gln Asn Ile His Ser
                125                 130

Leu Ser Pro Gln Glu Arg Glu Gln Phe Leu Gly Ala
            135                 140

Leu Asp Leu Ala Lys Lys Arg Val His Pro Asp Tyr
145                 150                 155

Val Ile Thr Thr Gln His Trp Leu Gly Leu Leu Gly
                160                 165

Pro Asn Gly Thr Gln Pro Gln Phe Ala Asn Cys Ser
        170                 175                 180

Val Tyr Asp Phe Phe Val Trp Leu His Tyr Tyr Ser
                185                 190
```

-continued

```
Val Arg Asp Thr Leu Leu Gly Pro Gly Arg Pro Tyr
    195                 200
Arg Ala Ile Asp Phe Ser His Gln Gly Pro Ala Phe
205             210                 215
Val Thr Trp His Arg Tyr His Leu Leu Cys Leu Glu
            220                 225
Arg Asp Leu Gln Arg Leu Ile Gly Asn Glu Ser Phe
    230                 235                 240
Ala Leu Pro Tyr Trp Asn Phe Ala Thr Gly Arg Asn
            245                 250
Glu Cys Asp Val Cys Thr Asp Gln Leu Phe Gly Ala
        255                 260
Ala Arg Pro Asp Asp Pro Thr Leu Ile Ser Arg Asn
265             270                 275
Ser Arg Phe Ser Ser Trp Glu Thr Val Cys Asp Ser
            280                 285
Leu Asp Asp Tyr Asn His Leu Val Thr Leu Cys Asn
    290                 295                 300
Gly Thr Tyr Glu Gly Leu Leu Arg Arg Asn Gln Met
                305                 310
Gly Arg Asn Ser Met Lys Leu Pro Thr Leu Lys Asp
            315                 320
Ile Arg Asp Cys Leu Ser Leu Gln Lys Phe Asp Asn
325             330                 335
Pro Pro Phe Phe Gln Asn Ser Thr Phe Ser Phe Arg
            340                 345
Asn Ala Leu Glu Gly Phe Asp Lys Ala Asp Gly Thr
        350                 355                 360
Leu Asp Ser Gln Val Met Ser Leu His Asn Leu Val
                365                 370
His Ser Phe Leu Asn Gly Thr Asn Ala Leu Pro His
            375                 380
Ser Ala Ala Asn Asp Pro Ile Phe Val Val Leu His
385             390                 395
Ser Phe Thr Asp Ala Ile Phe Asp Glu Trp Met Lys
            400                 405
Arg Phe Asn Pro Pro Ala Asp Ala Trp Pro Gln Glu
        410                 415                 420
Leu Ala Pro Ile Gly His Asn Arg Met Tyr Asn Met
                425                 430
Val Pro Phe Phe Pro Pro Val Thr Asn Glu Glu Leu
            435                 440
Phe Leu Thr Ser Asp Gln Leu Gly Tyr Ser Tyr Ala
445                 450                 455
Ile Asp Leu Pro Val Ser Val Glu Glu Thr Pro Gly
            460                 465
Trp Pro Thr Thr Leu Leu Val Val Met Gly Thr Leu
        470                 475                 480
Val Ala Leu Val Gly Leu Phe Val Leu Leu Ala Phe
                485                 490
Leu Gln Tyr Arg Arg Leu Arg Lys Gly Tyr Thr Pro
            495                 500
```

```
Leu Met Glu Thr His Leu Ser Ser Lys Arg Tyr Thr
505                 510                 515

Glu Glu Ala (2) INFORMATION FOR SEQ ID NO:3:

(i) SEQUENCE CHARACTERISTICS:
        (A) LENGTH:  11
        (B) TYPE:  AMINO ACID
        (C) STRANDEDNESS: SINGLE
        (D) TOPOLOGY:  UNKNOWN (ii) MOLECULE TYPE:
        (A) DESCRIPTION: PEPTIDE (ix) FEATURE:
        (A) NAME/KEY: TRP-2 PEPTIDE
        (B) LOCATION:
        (C) IDENTIFICATION METHOD:
        (D) OTHER INFORMATION:

(xi) SEQUENCE DESCRIPTION:SEQ ID NO:3:

Xaa Leu Leu Gly Pro Gly Arg Pro Tyr Arg Xaa
1               5                   10

(2) INFORMATION FOR SEQ ID NO:4:

(i) SEQUENCE CHARACTERISTICS:
        (A) LENGTH:  9
        (B) TYPE:  AMINO ACID
        (C) STRANDEDNESS: SINGLE
        (D) TOPOLOGY:  UNKNOWN (ii) MOLECULE TYPE:
        (A) DESCRIPTION: PEPTIDE (ix) FEATURE:
        (A) NAME/KEY: TRP-2 PEPTIDE
        (B) LOCATION:
        (C) IDENTIFICATION METHOD:
        (D) OTHER INFORMATION:

(xi) SEQUENCE DESCRIPTION:SEQ ID NO:4:

Leu Leu Gly Pro Gly Arg Pro Tyr Arg
1               5

(2) INFORMATION FOR SEQ ID NO:5:

(i) SEQUENCE CHARACTERISTICS:
        (A) LENGTH:  10
        (B) TYPE:  AMINO ACID
        (C) STRANDEDNESS: SINGLE
        (D) TOPOLOGY:  UNKNOWN (ii) MOLECULE TYPE:
        (A) DESCRIPTION: PEPTIDE (ix) FEATURE:
        (A) NAME/KEY: TRP-2 PEPTIDE
        (B) LOCATION:
        (C) IDENTIFICATION METHOD:
        (D) OTHER INFORMATION:

(xi) SEQUENCE DESCRIPTION:SEQ ID NO:5:

Thr Leu Leu Gly Pro Gly Arg Pro Tyr Arg
1               5                   10
```

```
(2) INFORMATION FOR SEQ ID NO:6:

(i) SEQUENCE CHARACTERISTICS:
        (A) LENGTH:  10
        (B) TYPE:  AMINO ACID
        (C) STRANDEDNESS:  SINGLE
        (D) TOPOLOGY:  UNKNOWN (ii) MOLECULE TYPE:
        (A) DESCRIPTION: PEPTIDE (ix) FEATURE:
        (A) NAME/KEY: TRP-2 PEPTIDE
        (B) LOCATION:
        (C) IDENTIFICATION METHOD:
        (D) OTHER INFORMATION:

(xi) SEQUENCE DESCRIPTION:SEQ ID NO:6:

Leu Leu Gly Pro Gly Arg Pro Tyr Arg Ala
1               5                   10

(2) INFORMATION FOR SEQ ID NO:7:

(i) SEQUENCE CHARACTERISTICS:
        (A) LENGTH:  9
        (B) TYPE:  AMINO ACID
        (C) STRANDEDNESS:  SINGLE
        (D) TOPOLOGY:  UNKNOWN (ii) MOLECULE TYPE:
        (A) DESCRIPTION: PEPTIDE (ix) FEATURE:
        (A) NAME/KEY: TRP-2 PEPTIDE VARIANT
        (B) LOCATION:
        (C) IDENTIFICATION METHOD:
        (D) OTHER INFORMATION:

(xi) SEQUENCE DESCRIPTION:SEQ ID NO:7:

Leu Ile Gly Pro Gly Arg Pro Tyr Arg
1               5

(2) INFORMATION FOR SEQ ID NO:8:

(i) SEQUENCE CHARACTERISTICS:
        (A) LENGTH:  9
        (B) TYPE:  AMINO ACID
        (C) STRANDEDNESS:  SINGLE
        (D) TOPOLOGY:  UNKNOWN (ii) MOLECULE TYPE:
        (A) DESCRIPTION: PEPTIDE (ix) FEATURE:
        (A) NAME/KEY: TRP-2 PEPTIDE VARIANT
        (B) LOCATION:
        (C) IDENTIFICATION METHOD:
        (D) OTHER INFORMATION:

(xi) SEQUENCE DESCRIPTION:SEQ ID NO:8:

Leu Val Gly Pro Gly Arg Pro Tyr Arg
1               5

(2) INFORMATION FOR SEQ ID NO:9:

(i) SEQUENCE CHARACTERISTICS:
        (A) LENGTH:  9
        (B) TYPE:  AMINO ACID
        (C) STRANDEDNESS:  SINGLE
        (D) TOPOLOGY:  UNKNOWN (ii) MOLECULE TYPE:
        (A) DESCRIPTION: PEPTIDE
```

```
    (ix) FEATURE:
         (A) NAME/KEY: TRP-2 PEPTIDE VARIANT
         (B) LOCATION:
         (C) IDENTIFICATION METHOD:
         (D) OTHER INFORMATION:

(xi) SEQUENCE DESCRIPTION:SEQ ID NO:9:

Leu Ser Gly Pro Gly Arg Pro Tyr Arg
1               5

(2) INFORMATION FOR SEQ ID NO:10:

(i) SEQUENCE CHARACTERISTICS:
        (A) LENGTH:  9
        (B) TYPE:  AMINO ACID
        (C) STRANDEDNESS:  SINGLE
        (D) TOPOLOGY:  UNKNOWN (ii) MOLECULE TYPE:
         (A) DESCRIPTION: PEPTIDE (ix) FEATURE:
         (A) NAME/KEY: TRP-2 PEPTIDE VARIANT
         (B) LOCATION:
         (C) IDENTIFICATION METHOD:
         (D) OTHER INFORMATION:

(xi) SEQUENCE DESCRIPTION:SEQ ID NO:10:

Leu Ala Gly Pro Gly Arg Pro Tyr Arg
1               5

(2) INFORMATION FOR SEQ ID NO:11:

(i) SEQUENCE CHARACTERISTICS:
        (A) LENGTH:  9
        (B) TYPE:  AMINO ACID
        (C) STRANDEDNESS:  SINGLE
        (D) TOPOLOGY:  UNKNOWN (ii) MOLECULE TYPE:
         (A) DESCRIPTION: PEPTIDE (ix) FEATURE:
         (A) NAME/KEY: TRP-2 PEPTIDE VARIANT
         (B) LOCATION:
         (C) IDENTIFICATION METHOD:
         (D) OTHER INFORMATION:

(xi) SEQUENCE DESCRIPTION:SEQ ID NO:11:

Leu Leu Gly Pro Gly Arg Pro Tyr Lys
1               5

(2) INFORMATION FOR SEQ ID NO:12:

(i) SEQUENCE CHARACTERISTICS:
        (A) LENGTH:  9
        (B) TYPE:  AMINO ACID
        (C) STRANDEDNESS:  SINGLE
        (D) TOPOLOGY:  UNKNOWN (ii) MOLECULE TYPE:
         (A) DESCRIPTION: PEPTIDE (ix) FEATURE:
         (A) NAME/KEY: TRP-2 PEPTIDE VARIANT
         (B) LOCATION:
         (C) IDENTIFICATION METHOD:
         (D) OTHER INFORMATION:

(xi) SEQUENCE DESCRIPTION:SEQ ID NO:12:

Lys Leu Gly Pro Gly Arg Pro Tyr Arg
1               5
```

(2) INFORMATION FOR SEQ ID NO:13:

(i) SEQUENCE CHARACTERISTICS:
        (A) LENGTH: 9
        (B) TYPE: AMINO ACID
        (C) STRANDEDNESS: SINGLE
        (D) TOPOLOGY: UNKNOWN (ii) MOLECULE TYPE:
        (A) DESCRIPTION: PEPTIDE (ix) FEATURE:
        (A) NAME/KEY: TRP-2 PEPTIDE VARIANT
        (B) LOCATION:
        (C) IDENTIFICATION METHOD:
        (D) OTHER INFORMATION:

(xi) SEQUENCE DESCRIPTION:SEQ ID NO:13:

Leu Leu Gly Pro Gly Phe Pro Tyr Arg
1               5

(2) INFORMATION FOR SEQ ID NO:14:

(i) SEQUENCE CHARACTERISTICS:
        (A) LENGTH: 9
        (B) TYPE: AMINO ACID
        (C) STRANDEDNESS: SINGLE
        (D) TOPOLOGY: UNKNOWN (ii) MOLECULE TYPE:
        (A) DESCRIPTION: PEPTIDE (ix) FEATURE:
        (A) NAME/KEY: TRP-2 PEPTIDE VARIANT
        (B) LOCATION:
        (C) IDENTIFICATION METHOD:
        (D) OTHER INFORMATION:

(xi) SEQUENCE DESCRIPTION:SEQ ID NO:14:

Leu Leu Gly Pro Gly Lys Pro Tyr Arg
1               5

(2) INFORMATION FOR SEQ ID NO:15:

(i) SEQUENCE CHARACTERISTICS:
        (A) LENGTH: 27
        (B) TYPE: NUCLEIC ACID
        (C) STRANDEDNESS: UNKNOWN
        (D) TOPOLOGY: UNKNOWN (ii) MOLECULE TYPE:
        (A) DESCRIPTION: OLIGONUCLEOTIDE (ix) FEATURE:
        (A) NAME/KEY:
        (B) LOCATION:
        (C) IDENTIFICATION METHOD:
        (D) OTHER INFORMATION: NUCLEIC ACID ENCODING
            TRP-2 PEPTIDE.

(xi) SEQUENCE DESCRIPTION:SEQ ID NO:15:

TTATTAGGAC CAGGACGCCC CTACAGG                                              27

(2) INFORMATION FOR SEQ ID NO:16:

(i) SEQUENCE CHARACTERISTICS:
        (A) LENGTH: 9
        (B) TYPE: AMINO ACID
        (C) STRANDEDNESS: UNKNOWN
        (D) TOPOLOGY: UNKNOWN (ii) MOLECULE TYPE:
        (A) DESCRIPTION: PEPTIDE (ix) FEATURE:
        (A) NAME/KEY:
        (B) LOCATION:
        (C) IDENTIFICATION METHOD:
        (D) OTHER INFORMATION:

(xi) SEQUENCE DESCRIPTION:SEQ ID NO:16:

Val Trp Leu His Tyr Tyr Ser Val Arg
1               5

(2) INFORMATION FOR SEQ ID NO:17:

(i) SEQUENCE CHARACTERISTICS:
        (A) LENGTH: 10
        (B) TYPE:  AMINO ACID
        (C) STRANDEDNESS:  UNKNOWN
        (D) TOPOLOGY:  UNKNOWN (ii) MOLECULE TYPE:
        (A) DESCRIPTION:  PEPTIDE (ix) FEATURE:
        (A) NAME/KEY:
        (B) LOCATION:
        (C) IDENTIFICATION METHOD:
        (D) OTHER INFORMATION:

(xi) SEQUENCE DESCRIPTION:SEQ ID NO:17:

Phe Val Trp Leu His Tyr Tyr Ser Val Arg
1               5                   10

(2) INFORMATION FOR SEQ ID NO:18:

(i) SEQUENCE CHARACTERISTICS:
        (A) LENGTH: 9
        (B) TYPE:  AMINO ACID
        (C) STRANDEDNESS:  UNKNOWN
        (D) TOPOLOGY:  UNKNOWN (ii) MOLECULE TYPE:
        (A) DESCRIPTION:  PEPTIDE (ix) FEATURE:
        (A) NAME/KEY:
        (B) LOCATION:
        (C) IDENTIFICATION METHOD:
        (D) OTHER INFORMATION:

(xi) SEQUENCE DESCRIPTION:SEQ ID NO:18:

Arg Asp Thr Leu Leu Gly Pro Gly Arg
1               5

(2) INFORMATION FOR SEQ ID NO:19:

(i) SEQUENCE CHARACTERISTICS:
        (A) LENGTH: 9
        (B) TYPE:  AMINO ACID
        (C) STRANDEDNESS:  UNKNOWN
        (D) TOPOLOGY:  UNKNOWN (ii) MOLECULE TYPE:
        (A) DESCRIPTION:  PEPTIDE (ix) FEATURE:
        (A) NAME/KEY:
        (B) LOCATION:
        (C) IDENTIFICATION METHOD:
        (D) OTHER INFORMATION:

(xi) SEQUENCE DESCRIPTION:SEQ ID NO:19:

Gly Pro Ala Phe Val Thr Trp His Arg
1               5

```
(2) INFORMATION FOR SEQ ID NO:20:

(i) SEQUENCE CHARACTERISTICS:
        (A) LENGTH: 9
        (B) TYPE:  AMINO ACID
        (C) STRANDEDNESS:  UNKNOWN
        (D) TOPOLOGY:  UNKNOWN (ii) MOLECULE TYPE:
        (A) DESCRIPTION:  PEPTIDE (ix) FEATURE:
        (A) NAME/KEY:
        (B) LOCATION:
        (C) IDENTIFICATION METHOD:
        (D) OTHER INFORMATION:

(xi) SEQUENCE DESCRIPTION:SEQ ID NO:20:

Met Ser Leu Gln Arg Gln Phe Leu Arg
1               5

(2) INFORMATION FOR SEQ ID NO:21:

(i) SEQUENCE CHARACTERISTICS:
        (A) LENGTH: 9
        (B) TYPE:  AMINO ACID
        (C) STRANDEDNESS:  UNKNOWN
        (D) TOPOLOGY:  UNKNOWN (ii) MOLECULE TYPE:
        (A) DESCRIPTION:  PEPTIDE (ix) FEATURE:
        (A) NAME/KEY:
        (B) LOCATION:
        (C) IDENTIFICATION METHOD:
        (D) OTHER INFORMATION:

(xi) SEQUENCE DESCRIPTION:SEQ ID NO:21:

Leu Phe Gly Pro Gly Arg Pro Tyr Arg
1               5

(2) INFORMATION FOR SEQ ID NO:22:

(i) SEQUENCE CHARACTERISTICS:
        (A) LENGTH: 9
        (B) TYPE:  AMINO ACID
        (C) STRANDEDNESS:  UNKNOWN
        (D) TOPOLOGY:  UNKNOWN (ii) MOLECULE TYPE:
        (A) DESCRIPTION:  PEPTIDE (ix) FEATURE:
        (A) NAME/KEY:
        (B) LOCATION:
        (C) IDENTIFICATION METHOD:
        (D) OTHER INFORMATION:

(xi) SEQUENCE DESCRIPTION:SEQ ID NO:22:

Leu Leu Gly Pro Gly Arg Pro Tyr His
1               5

(2) INFORMATION FOR SEQ ID NO:23:

(i) SEQUENCE CHARACTERISTICS:
        (A) LENGTH: 9
        (B) TYPE:  AMINO ACID
        (C) STRANDEDNESS:  UNKNOWN
        (D) TOPOLOGY:  UNKNOWN (ii) MOLECULE TYPE:
        (A) DESCRIPTION:  PEPTIDE
```

```
        (ix) FEATURE:
              (A) NAME/KEY:
              (B) LOCATION:
              (C) IDENTIFICATION METHOD:
              (D) OTHER INFORMATION:

(xi) SEQUENCE DESCRIPTION:SEQ ID NO:23:

Ala Leu Gly Pro Gly Arg Pro Tyr Arg
1               5

(2) INFORMATION FOR SEQ ID NO:24:

(i) SEQUENCE CHARACTERISTICS:
              (A) LENGTH: 9
              (B) TYPE:  AMINO ACID
              (C) STRANDEDNESS:  UNKNOWN
              (D) TOPOLOGY:  UNKNOWN (ii) MOLECULE TYPE:
              (A) DESCRIPTION:  PEPTIDE (ix) FEATURE:
              (A) NAME/KEY:
              (B) LOCATION:
              (C) IDENTIFICATION METHOD:
              (D) OTHER INFORMATION:

(xi) SEQUENCE DESCRIPTION:SEQ ID NO:24:

Arg Leu Gly Pro Gly Arg Pro Tyr Arg
1               5

(2) INFORMATION FOR SEQ ID NO:25:

(i) SEQUENCE CHARACTERISTICS:
              (A) LENGTH: 9
              (B) TYPE:  AMINO ACID
              (C) STRANDEDNESS:  UNKNOWN
              (D) TOPOLOGY:  UNKNOWN (ii) MOLECULE TYPE:
              (A) DESCRIPTION:  PEPTIDE (ix) FEATURE:
              (A) NAME/KEY:
              (B) LOCATION:
              (C) IDENTIFICATION METHOD:
              (D) OTHER INFORMATION:

(xi) SEQUENCE DESCRIPTION:SEQ ID NO:25:

Leu Leu Leu Pro Gly Arg Pro Tyr Arg
1               5

(2) INFORMATION FOR SEQ ID NO:26:

(i) SEQUENCE CHARACTERISTICS:
              (A) LENGTH: 9
              (B) TYPE:  AMINO ACID
              (C) STRANDEDNESS:  UNKNOWN
              (D) TOPOLOGY:  UNKNOWN (ii) MOLECULE TYPE:
              (A) DESCRIPTION:  PEPTIDE (ix) FEATURE:
              (A) NAME/KEY:
              (B) LOCATION:
              (C) IDENTIFICATION METHOD:
              (D) OTHER INFORMATION:

(xi) SEQUENCE DESCRIPTION:SEQ ID NO:26:

Leu Leu Phe Pro Gly Arg Pro Tyr Arg
1               5
```

```
(2) INFORMATION FOR SEQ ID NO:27:

(i) SEQUENCE CHARACTERISTICS:
        (A) LENGTH: 9
        (B) TYPE:  AMINO ACID
        (C) STRANDEDNESS:  UNKNOWN
        (D) TOPOLOGY:  UNKNOWN (ii) MOLECULE TYPE:
        (A) DESCRIPTION:  PEPTIDE (ix) FEATURE:
        (A) NAME/KEY:
        (B) LOCATION:
        (C) IDENTIFICATION METHOD:
        (D) OTHER INFORMATION:

(xi) SEQUENCE DESCRIPTION:SEQ ID NO:27:

Leu Leu Ala Pro Gly Arg Pro Tyr Arg
1               5

(2) INFORMATION FOR SEQ ID NO:28:

(i) SEQUENCE CHARACTERISTICS:
        (A) LENGTH: 9
        (B) TYPE:  AMINO ACID
        (C) STRANDEDNESS:  UNKNOWN
        (D) TOPOLOGY:  UNKNOWN (ii) MOLECULE TYPE:
        (A) DESCRIPTION:  PEPTIDE (ix) FEATURE:
        (A) NAME/KEY:
        (B) LOCATION:
        (C) IDENTIFICATION METHOD:
        (D) OTHER INFORMATION:

(xi) SEQUENCE DESCRIPTION:SEQ ID NO:28:

Leu Leu Gly Pro Gly Ala Pro Tyr Arg
1               5

(2) INFORMATION FOR SEQ ID NO:29:

(i) SEQUENCE CHARACTERISTICS:
        (A) LENGTH: 9
        (B) TYPE:  AMINO ACID
        (C) STRANDEDNESS:  UNKNOWN
        (D) TOPOLOGY:  UNKNOWN (ii) MOLECULE TYPE:
        (A) DESCRIPTION:  PEPTIDE (ix) FEATURE:
        (A) NAME/KEY:
        (B) LOCATION:
        (C) IDENTIFICATION METHOD:
        (D) OTHER INFORMATION:

(xi) SEQUENCE DESCRIPTION:SEQ ID NO:29:

Leu Leu Gly Pro Gly Ile Pro Tyr Arg
1               5

(2) INFORMATION FOR SEQ ID NO:30:

(i) SEQUENCE CHARACTERISTICS:
        (A) LENGTH: 9
        (B) TYPE:  AMINO ACID
        (C) STRANDEDNESS:  UNKNOWN
        (D) TOPOLOGY:  UNKNOWN (ii) MOLECULE TYPE:
        (A) DESCRIPTION:  PEPTIDE
```

-continued

```
   (ix) FEATURE:
         (A) NAME/KEY:
         (B) LOCATION:
         (C) IDENTIFICATION METHOD:
         (D) OTHER INFORMATION:

(xi) SEQUENCE DESCRIPTION:SEQ ID NO:30:

Leu Leu Gly Pro Gly Val Pro Tyr Arg
1               5

(2) INFORMATION FOR SEQ ID NO:31:

(i) SEQUENCE CHARACTERISTICS:
         (A) LENGTH: 9
         (B) TYPE:  AMINO ACID
         (C) STRANDEDNESS:  UNKNOWN
         (D) TOPOLOGY:  UNKNOWN (ii) MOLECULE TYPE:
         (A) DESCRIPTION:  PEPTIDE (ix) FEATURE:
         (A) NAME/KEY:  TRP-2 peptide Variant
         (B) LOCATION:  2 to 9
         (C) IDENTIFICATION METHOD:  Experimental
         (D) OTHER INFORMATION:  First Xaa is Ile, Ser,
             Leu, Val; Second Xaa is Lys or Arg (xi) SEQUENCE DESCRIPTION:SEQ ID NO:31:

Leu Xaa Gly Pro Gly Arg Pro Tyr Xaa
```